(12) United States Patent
Tamano et al.

(10) Patent No.: US 6,329,084 B1
(45) Date of Patent: *Dec. 11, 2001

(54) COMPOUND FOR ORGANIC ELECTRO-LUMINESCENCE DEVICE AND ORGANIC ELECTRO-LUMINESCENCE DEVICE USING THE COMPOUND

(75) Inventors: Michiko Tamano; Shinichiro Maki, both of Tokyo (JP)

(73) Assignee: Toyo Ink Mfg. Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/332,913

(22) Filed: Jun. 15, 1999

(30) Foreign Application Priority Data

Jun. 15, 1998 (JP) .................................................. 10-166459
Apr. 26, 1999 (JP) .................................................. 11-117451

(51) Int. Cl.$^7$ .......................... H05B 33/14; C09K 11/06; C07C 211/00
(52) U.S. Cl. .......................... 428/690; 428/917; 313/504; 313/506; 564/426; 564/429; 252/301.16
(58) Field of Search ..................................... 428/690, 704, 428/917; 313/502, 504, 506; 564/305, 426, 429, 431; 252/301.16

(56) References Cited

U.S. PATENT DOCUMENTS 4,618,694  10/1986  Iden et al. ............................. 558/416
6,013,383  * 1/2000  Shi et al. ............................. 428/690

FOREIGN PATENT DOCUMENTS 0 757 088  2/1997  (EP) .

OTHER PUBLICATIONS

Grant & Hackh's Chemical Dictionary, 5th ed., McGraw–Hill, Inc., p. 146, 1987.*

Patent Abstracts of Japan, 14(475) (C–0770) (Oct. 1990) (abstract of JP 2–196885).

Patent Abstracts of Japan, 16(249) (C–0948) (Jun. 1992) (abstract of JP 4–055493).

* cited by examiner

Primary Examiner—Marie Yamnitzky
(74) Attorney, Agent, or Firm—Wenderoth, Lind & Ponack, LLP

(57) ABSTRACT

Compounds for organic EL devices which emit light of red, have a high light emission brightness and have a long lifetime of light emission, and organic EL devices using the above compounds, the light-emitting materials being compounds of the formula [1],

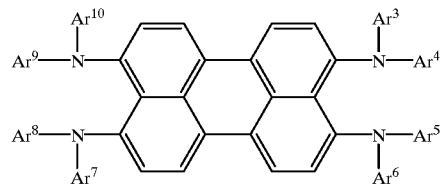

wherein each of $Ar^3$ to $Ar^{10}$ is independently a substituted or non-substituted aromatic monocyclic group, a substituted or non-substituted fused polycyclic group or a substituted or non-substituted aromatic heterocyclic group, provided that $Ar^3$ and $Ar^4$ may integrally bond to each other, that $Ar^5$ and $Ar^6$ may integrally bond to each other, that $Ar^7$ and $Ar^8$ may integrally bond to each other, and that $Ar^9$ and $Ar^{10}$ may integrally bond to each other.

8 Claims, 2 Drawing Sheets

COMPOUND FOR ORGANIC ELECTRO-LUMINESCENCE DEVICE AND ORGANIC ELECTRO-LUMINESCENCE DEVICE USING THE COMPOUND

FIELD OF THE INVENTION

The present invention relates to a compound for an organic electroluminescence (to be referred to as "EL" hereinafter) device for use in a flat panel or display, and a light-emitting device having a high brightness.

PRIOR ART OF THE INVENTION

An EL device using an organic substance is expected to be promising as a solid light-emitting inexpensive large-screen, full-color display device, and developments thereof are being made in many ways. Generally, an EL device is composed of a light-emitting layer and a pair of facing electrodes sandwiching the light-emitting layer. The light emission of an EL device is the following phenomenon. When an electric field is applied between the two electrodes, the cathode injects electrons into the light-emitting layer, and the anode injects holes into the light-emitting layer. The injected electrons recombine with the holes in the light-emitting layer, and their energy level shifts from a conduction band back to a valence bond band to release energy as light.

As compared with inorganic EL devices, conventional organic EL devices require high driving voltage, and their light emission brightness and light emission efficiency are low. Further, conventional organic EL devices deteriorate in properties to a great extent, and no organic EL device has been put to practical use.

In recent years, there has been proposed an organic EL device which is produced by laminating a thin film containing an organic compound having a fluorescent quantum effect of emitting light at a low voltage as low as less than 10 V, and it attracts attention (Appl. Phy. Lett., Vol. 51, page 913, 1987).

The above organic EL device has a light-emitting layer containing a metal chelate complex and a hole-injecting layer containing an amine-based compound, and emits green light having a high brightness. The above organic EL device achieves nearly practically usable performance, since it accomplishes a brightness of 1,000 cd/m$^2$ and a maximum light emission efficiency of 1.5 lm/W at a DC voltage of 6 to 10 V.

However, conventional organic EL devices including the above organic EL device are not yet satisfactory in brightness although these organic EL devices are improved in brightness to some extent. Further, they have a serious problem that their stability is poor in their continuous operation for a long period of time. That is because, for example, a metal chelate complex such as a tris(8-hydroxyquinolinate)-aluminum complex, or the like, is chemically unstable when an electric field is applied for light emission, is poor in adhesion to a cathode and extremely deteriorates in a short period of emission. For the above reasons, it is desired to develop a light-emitting material having an excellent light emission capacity and durability for developing an organic EL device which has a high light emission brightness and a high light emission efficiency and can perform a light emission in its continuous operation.

SUMMARY OF THE INVENTION

It is an object of the present invention to provide a compound for an organic EL device which shows red light emission colors, has a high light emission brightness and has a long lifetime of light emission, and organic EL device using the above compound.

According to the present invention, the above object of the present invention is achieved by any one of the following constitutions.

(1) A compound for an organic electroluminescence device, which comprises a compound of the formula [1],

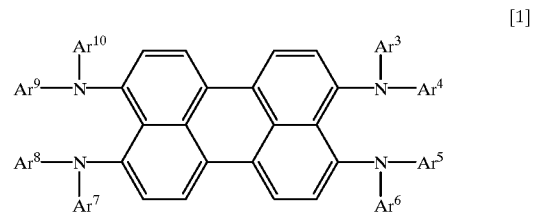

wherein each of Ar$^3$ to Ar$^{10}$ is independently a substituted or non-substituted aromatic monocyclic group, a substituted or non-substituted fused polycyclic group or a substituted or non-substituted aromatic heterocyclic group, provided that Ar$^3$ and Ar$^4$ may integrally bond to each other, that Ar$^5$ and Ar$^6$ may integrally bond to each other, that Ar$^7$ and Ar$^8$ may integrally bond to each other, and that Ar$^9$ and Ar$^{10}$ may integrally bond to each other.

(2) A light-emitting material for an organic electroluminescence device, which comprises the compound of the formula [1] recited in the above (1).

(3) A light-emitting material according to the above (2), which contains the compound of the formula [1] and a host material, the content of the compound of the formula [1] being 0.001 to 50% by weight based on the host material.

(4) A light-emitting material according to the above (3), wherein the host material is at least one material selected from the group consisting of an electron-injecting material, a hole-injecting material and an electrically conductive polymer.

(5) A light-emitting material according to the above (2), which contains at least two compounds selected from the compound of the formula [1] and a compound of the formula [2] respectively.

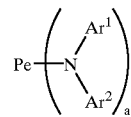

wherein Pe is a perylene residue, each of Ar$^1$ and Ar$^2$ is independently a substituted or non-substituted aryl group, a substituted or non-substituted fused polycyclic group, a substituted or non-substituted aromatic heterocyclic group, provided that Ar$^1$ and Ar$^2$ may integrally bond to each other, and a is an integer of 2 to 12, provided that the compound of the formula [2] does not include the compound of the formula [1].

(6) An organic electroluminescence device comprising a pair of electrodes composed of an anode and a cathode and an organic layer including at least one light-emitting layer, the organic layer being formed between a pair of the electrodes, the light-emitting layer containing the light-emitting material recited in the above (2).

(7) An organic electroluminescence device according to the above (6), wherein at least one electron-injecting layer is formed between the light-emitting layer and the cathode.

(8) An organic electroluminescence device according to the above (7), wherein the light-emitting layer or the electron-injecting layer contains a compound of the formula [3],

[3]

wherein each of $Q^1$ and $Q^2$ is independently a substituted or non-substituted hydroxyquinoline derivative or a substituted or non-substituted hydroxybenzoquinoline derivative, L is a halogen atom, a substituted or non-substituted alkyl group, a substituted or non-substituted cycloalkyl group, a substituted or non-substituted aryl group, a substituted or non-substituted aromatic heterocyclic group, or a ligand of —OR in which R is a hydrogen atom, a substituted or non-substituted alkyl group, a substituted or non-substituted cycloalkyl group, a substituted or non-substituted aryl group or a substituted or non-substituted aromatic heterocyclic group or —O—Ga—$Q^3(Q^4)$ in which $Q^3$ and $Q^4$ have the same meanings as those of $Q^1$ and $Q^2$.

DETAILED DESCRIPTION OF THE INVENTION

Figure 1:
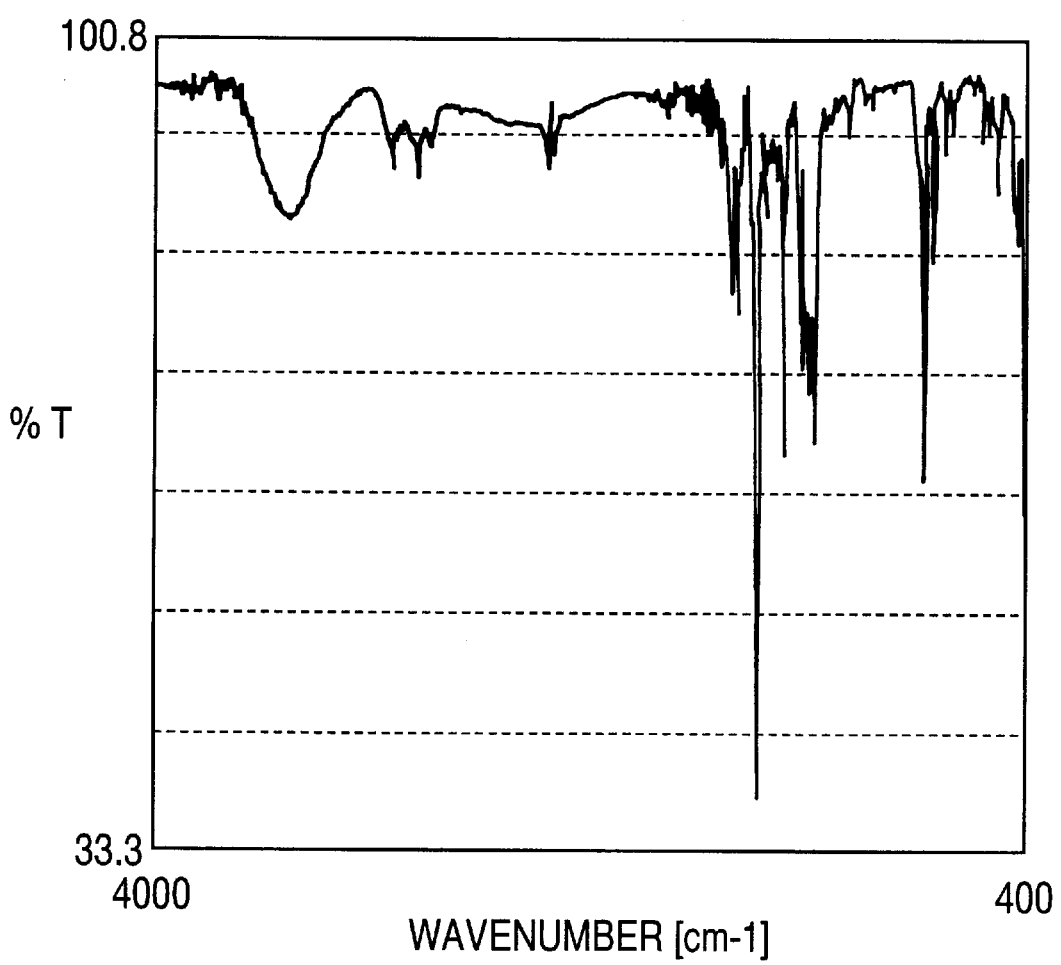
FIG. 1 shows an infrared absorption spectrum of Compound (1).

The present inventors have made diligent studies for achieving the above object, and have found that organic EL devices having light-emitting layers containing compounds of the formula [1] emit red light, have high light emission brightness and high light emission efficiency and have excellent light emission lives. Further, it has been found that an organic EL device having a light-emitting layer which contains a compound of the formula [1] and at least one hole-injecting layer which contains a compound of the formula [3] and is present between the light-emitting layer and a cathode can be a useful light-emitting device.

In the formula [2], Pe is a perylene residue. The perylene residue in the formula [1] and a perylene residue in the formula [2] may have a substituent such as a halogen atom, a cyano group, a substituted or non-substituted alkyl group, a substituted or non-substituted alkoxy group, a substituted or non-substituted aryloxy group, a substituted or non-substituted alkylthio group, a substituted or non-substituted arylthio group, a substituted or non-substituted aryl group or a substituted or non-substituted aromatic heterocylic group.

In the formulae [1] and [2], each of $Ar^1$ to $Ar^{10}$ is independently a substituted or non-substituted phenyl group, a substituted or non-substituted fused polycyclic group or a substituted or non-substituted aromatic heterocyclic group.

The substituted or non-substituted aryl group includes those phenyl groups having substituents.

The substituted or non-substituted fused polycyclic group includes heterocyclic-group-free aromatic groups such as naphtyl, anthryl, phenanthryl, pirenyl, perylenyl and triphenyl, and it may have a substituent.

The substituted or non-substituted aromatic heterocyclic group includes substituted or non-substituted aromatic heterocyclic groups having 2 to 3 carbon atoms such as pyridyl, pyrazinyl, pyrimidinyl, pyridazinyl, triazinyl, indolinyl, quinolyl, acrydinyl, carbozolyl, furyl, thiophenyl, oxazolyl, oxadiazolyl, benzoxadiazolyl, thiazolyl, thiaziazolyl, benzothiazoyl, trizolyl, benzotriazolyl, imidazolyl and benzimidazolyl, and it may have a substituent.

$Ar^1$ and $Ar^2$ may bond to each other to form a new heteroyclic ring, $Ar^3$ and $Ar^4$ may bond to each other to form a new heteroyclic ring, that $Ar^5$ and $Ar^6$ may bond to each other to form a new heteroyclic ring, that $Ar^7$ and $Ar^8$ may bond to each other to form a new heteroyclic ring, and that $Ar^9$ and $Ar^{10}$ may bond to each other to form a new heteroyclic ring. The heterocyclic ring includes a pyrrolidine ring, a pyrazolidine ring, piperidine ring, a morpholine ring, piperazine ring, a tritian ring and the above aromatic heterocyclic groups.

In the present invention, substituents are independently a hydrogen atom, a halogen atom, a cyano group, a nitro group, a substituted or non-substituted alkyl group, a substituted or non-substituted alkoxy group, a substituted or non-substituted aryloxy group, a substituted or non-substituted alkylthio group, a substituted or non-substituted aryl group, a substituted or non-substituted aromatic heterocyclic group or —$NR^6R^7$ in which each of $R^6$ and $R^7$ is a substituted or non-substituted alkyl group, a substituted or non-substituted aryl group or a substituted or non-substituted aromatic heterocyclic group, provided that $R^6$ and $R^7$ may integrally bond to each other.

The above substituted or non-substituted alkyl group includes alkyl groups having 1 to 30 carbon atoms such as methyl, ethyl, propyl, butyl, sec-butyl, tert-butyl, pentyl, hexyl, heptyl, octyl, stearyl, 2-phenylisopropyl, trichloromethyl, trifluoromethyl, benzyl, α-phenoxybenzyl, α,α-dimethylbenzyl, α,α-methylphenylbenzyl, α,α-ditrifluoromethylbenzyl, tripehnylmethyl and α-benzyloxybenzyl.

The substituted or non-substituted alkoxy group includes alkoxy groups having 1 to 20 carbon atoms such as methoxy, ethoxy, propoxy, n-butyoxy, t-butoxy, n-octyloxyl, t-octyloxy, 1,1,1-tetrafluoroethoxy, benzyloxy and octylphenoxy.

The substituted or non-substituted alkylthio group includes methylthio, ethylthio, tert-butylthio, hexylthio, octylthio and trifluoromethylthio.

The substituted or non-substituted aryloxy group includes phenoxy, 4-nitrophenoxy, tert-butylphenoxy, 3-fluorophenoxy, pentafluorophenyl and trifluoromethylphenoxy.

The substituted or non-substituted arylthio group includes phenylthio, 4-methylphenylthio, tert-butylphenylthio, 3-fluorophenylthio, pentafluorophenylthio and 3-trifluoromethylphenylthio.

The substituted or non-substituted aryl group includes phenyl, naphthyl, anthryl, phenanthryl, fluorenyl, pirenyl, perylenyl and triphenylenyl. These may have a substituent.

Specific examples of the —NR⁶R⁷ (in which each of $R^6$ and $R^7$ is a substituted or non-substituted alkyl group) include ethylamino, dimethylamino, dipropylamino, dibutylamino, benzylamino, dibenzylamino, (3-methylphenyl)amino, (4-methylphenyl)amino, phenylamino, phenylmethylamino, diphenylamino, ditolylamino, dipyridylamino, phenylthiophenylamino, dibiphenylamino, di(4-methylbiphenyl)amino, di(3-methylphenyl)amino, di(4-methylphenyl)amino, naphthylphenylamino and bis[4-(α,α'-dimethylbenzyl)phenyl]amino.

Of the above substituents, alkyl, alkoxy and diphenylamino are preferred.

In the present invention, combinations of at least two compounds selected from the formulae [1] and [2] respectively are useful since the colors of emitted light can be red-shifted.

Typical examples of the above combinations are shown in Table 1, such as a combination of structural isomers like Compounds (2) and (49) and a combination of Compounds (63) and (53). Examples of a combination of three compounds include combinations of three compounds in Table 1, such as a combination of isomers like Compounds (1), (2) and (49) and a combination of Compounds (18), (19) and (60).

The compound of the formula [1] or [2] which has a perylene ring has a high glass transition point and a high melting point and therefore has high durability (heat resistance) against Joule heat generated in an organic layer or an intermediate layer or between an organic layer and a metal electrode during the light emission by an electric field. When used as a light-emitting material for an organic EL device, therefore, the above compound exhibits a high light emission brightness and is therefore advantageous for the lifetime of light emission. The compound of the present invention shall not be limited to substituents.

The compound of the formula [1] or [2] can be produced, e.g., by the following method. In one method, halogenated perylene and an aromatic diamine compound are allowed to react in an inert solvent in the presence of a catalyst such as copper at 200° C. for a long period of time. In another method, aminoperylene and a halogenated aryl compound are allowed to react in an inert solvent. As a catalyst, a copper powder, cuprous chloride, tin or stannous chloride is used. The solvent is selected from N,N-dimethylformamide or dimethylsulfoxide.

When the compounds of the formula [1] are used as light-emitting materials of organic EL devices, the devices exhibit a high light emission efficiency in a broad light emission region of red.

Most of the compounds of the formula [2] have a melting point of 300° C. or higher and have a high light emission brightness, and they are remarkably useful for producing devices having a long lifetime. Further, it is preferred to use a combination of the compound of the formula [1] with the compound of the formula [2]. In this case, it is particularly preferred to use the compound of the formula [2] in which a is 2.

Although not specially limited, typical examples of the compound of the formula [1] or [2] are specifically shown in Table 1.

The compounds corresponding to the formula [1] are (49), (52), (53), (55)–(61) and (65).

TABLE 1

| Compound | Chemical structure |
|---|---|
| (1) | 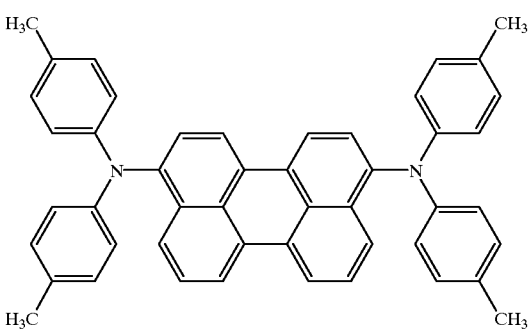 |

TABLE 1-continued
| Compound | Chemical structure |
|---|---|
| (2) | 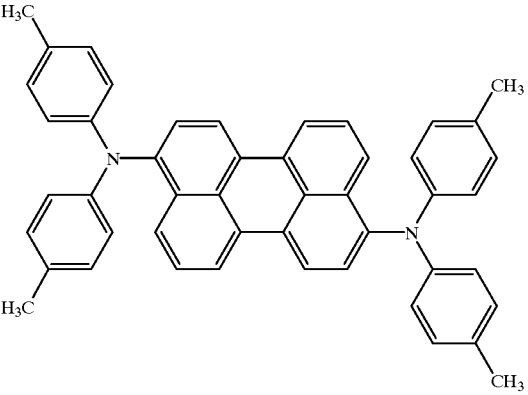 |
| (3) | 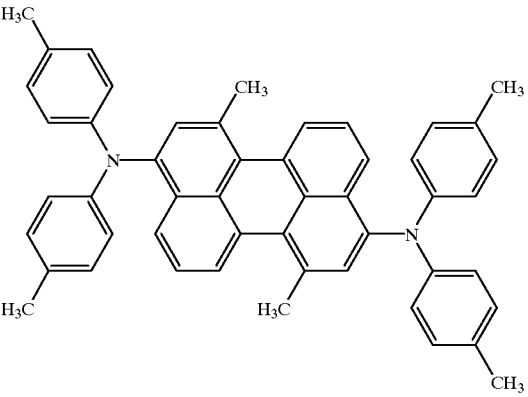 |
| (4) | 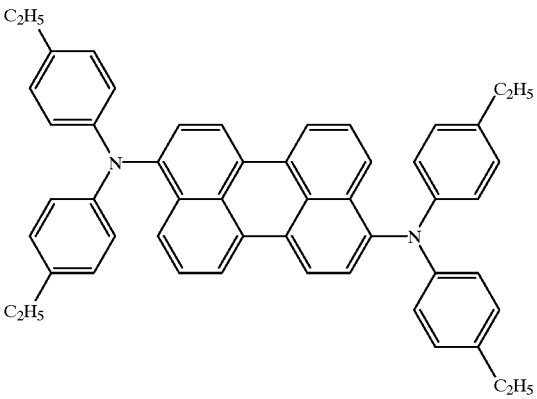 |

TABLE 1-continued
| Compound | Chemical structure |
|---|---|
| (5) | 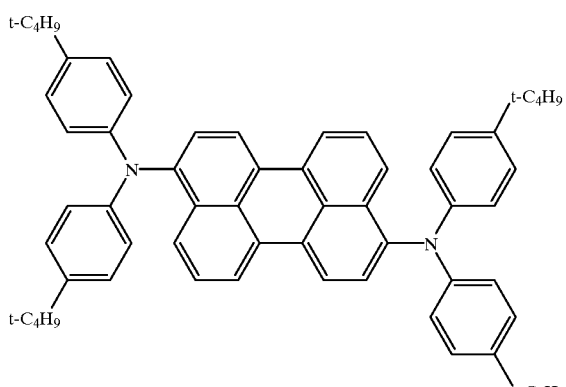 |
| (6) | 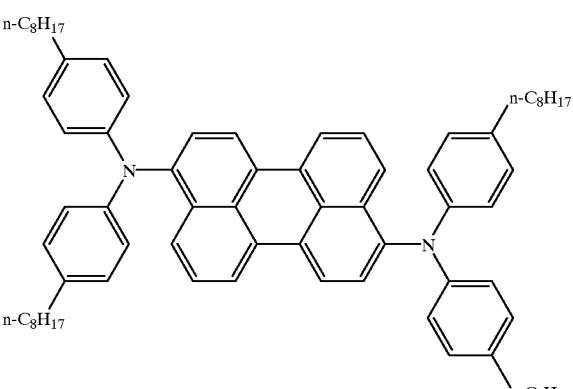 |
| (7) | 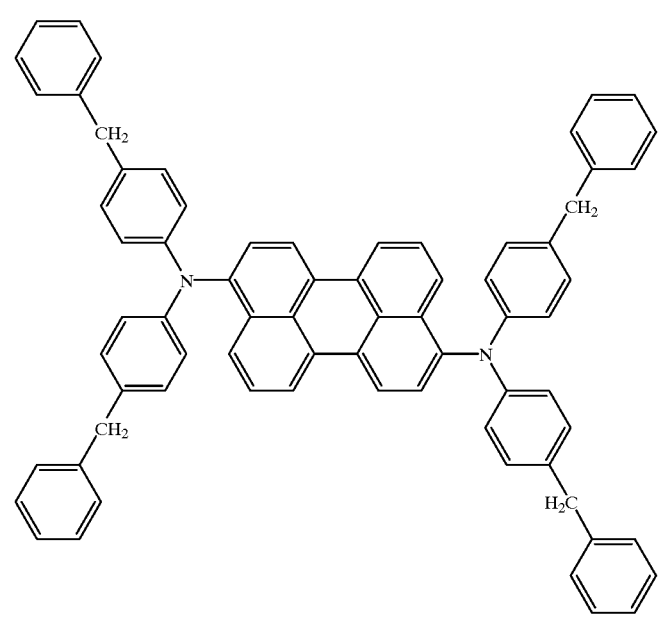 |

TABLE 1-continued
| Compound | Chemical structure |
| --- | --- |
| (8) | 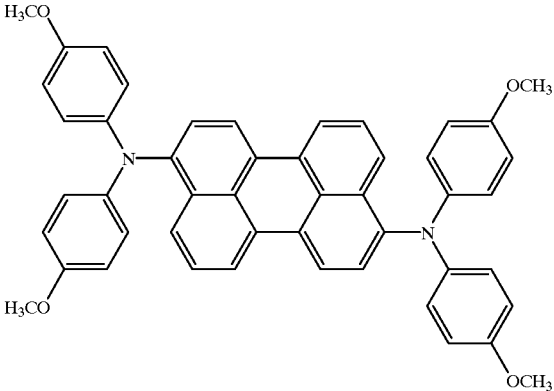 |
| (9) | 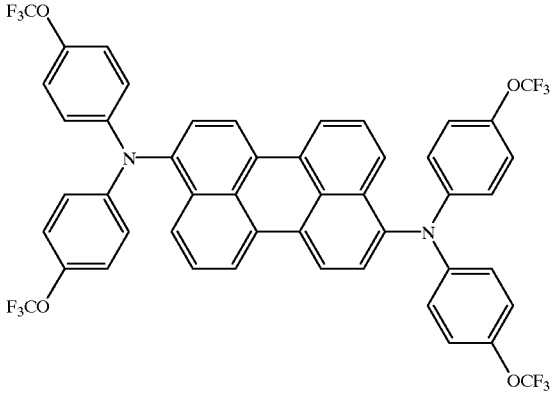 |
| (10) | 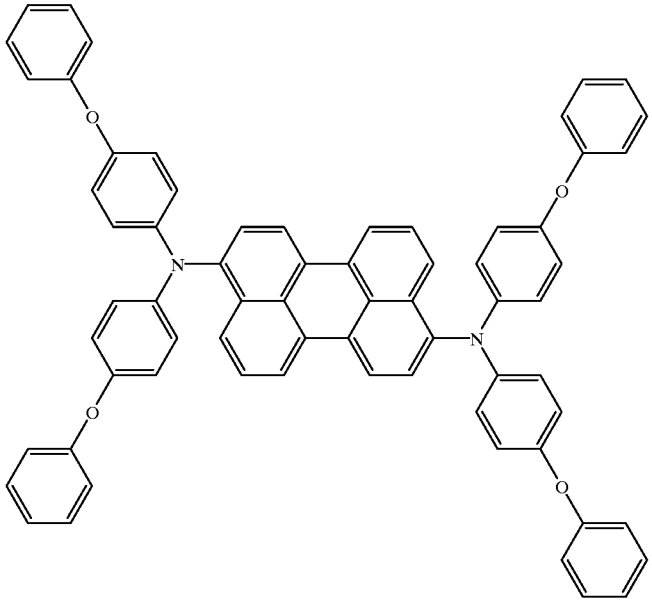 |

TABLE 1-continued

| Compound | Chemical structure |
|---|---|
| (11) | 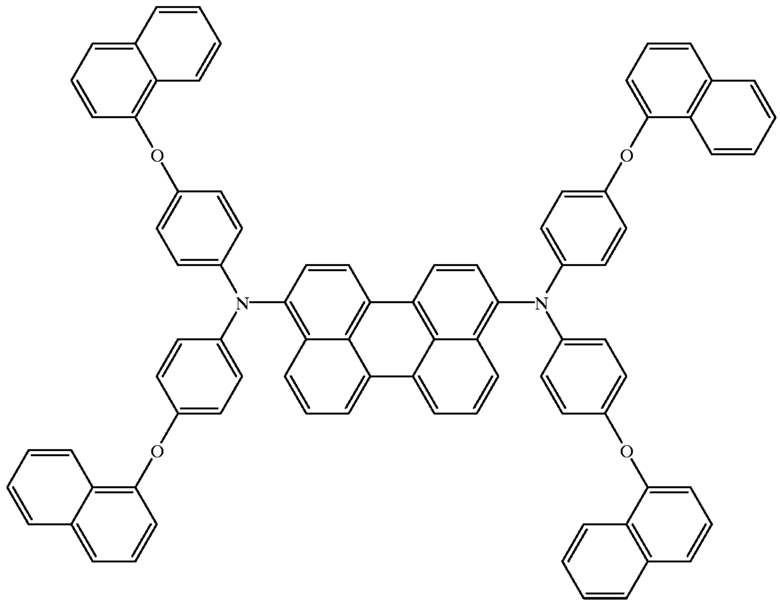 |
| (12) | 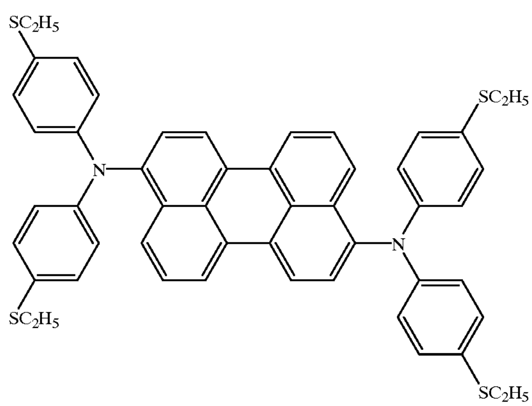 |

TABLE 1-continued

| Compound | Chemical structure |
|---|---|
| (13) | 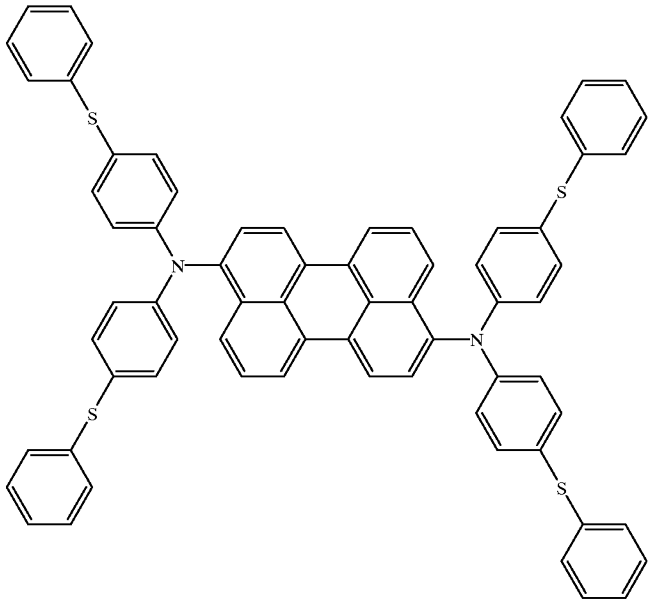 |
| (14) | 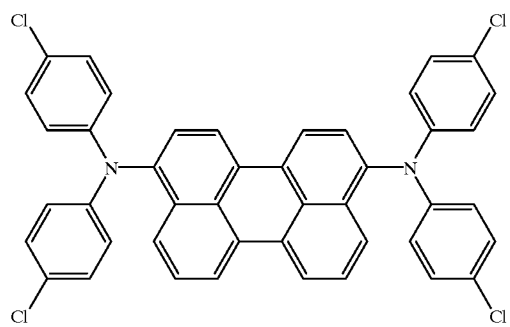 |
| (15) | 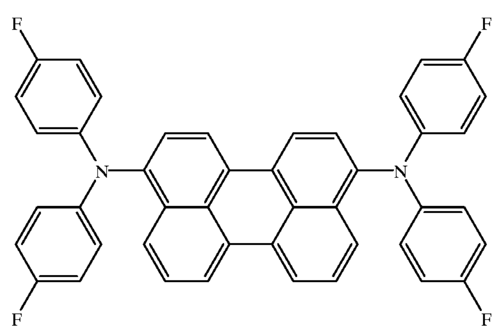 |

TABLE 1-continued

| Compound | Chemical structure |
| --- | --- |
| (16) | 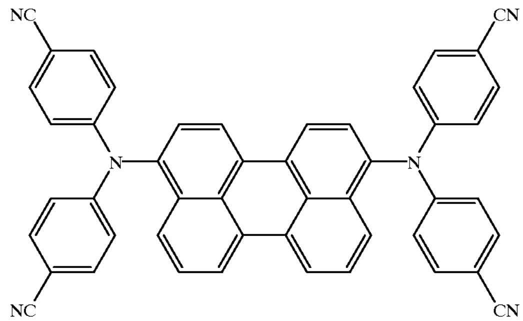 |
| (17) | 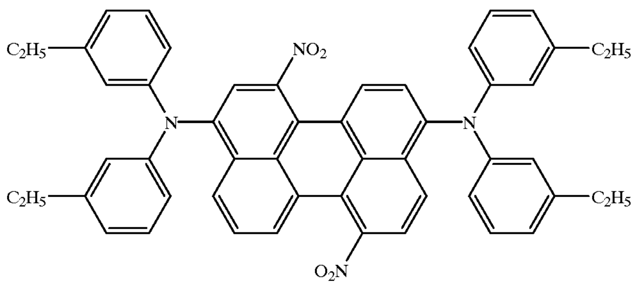 |
| (18) | 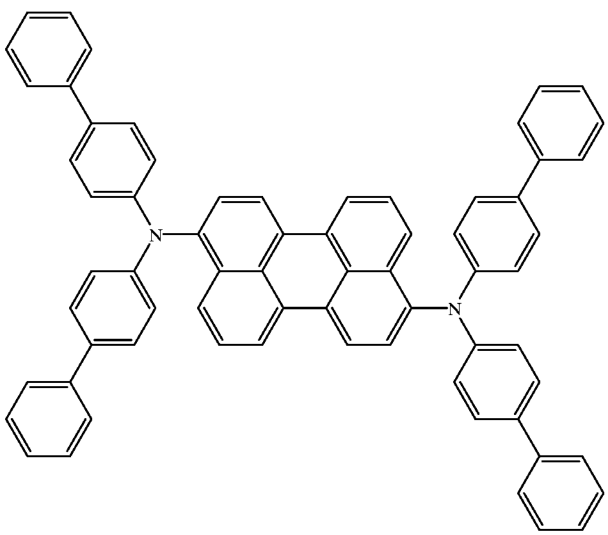 |
| (19) | 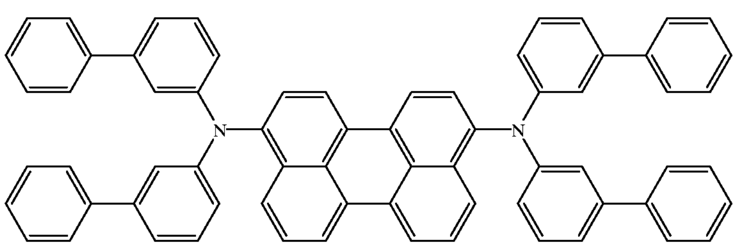 |

TABLE 1-continued
| Compound | Chemical structure |
|---|---|
| (20) | 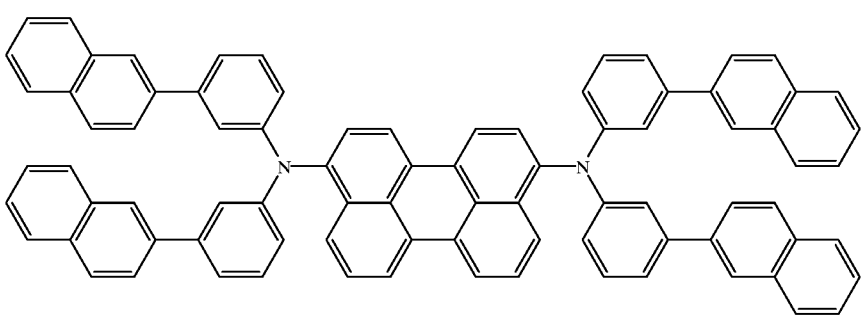 |
| (21) | 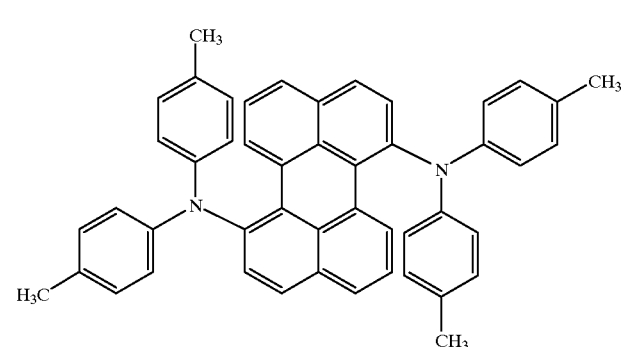 |
| (22) | 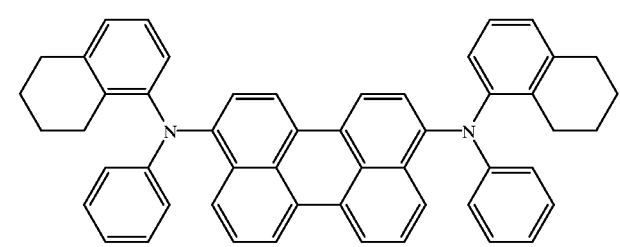 |
| (23) | 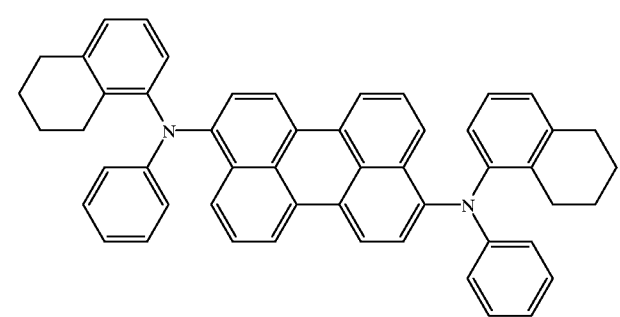 |
| (24) | 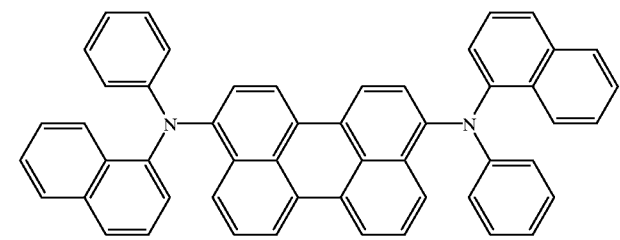 |

TABLE 1-continued

| Compound | Chemical structure |
| --- | --- |
| (25) | 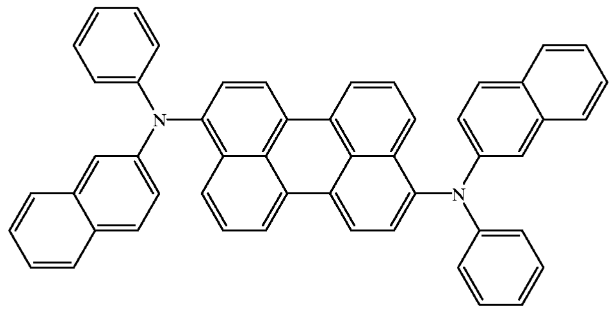 |
| (26) | 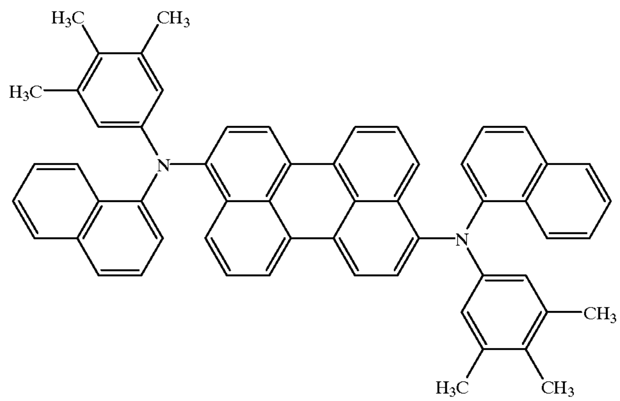 |
| (27) | 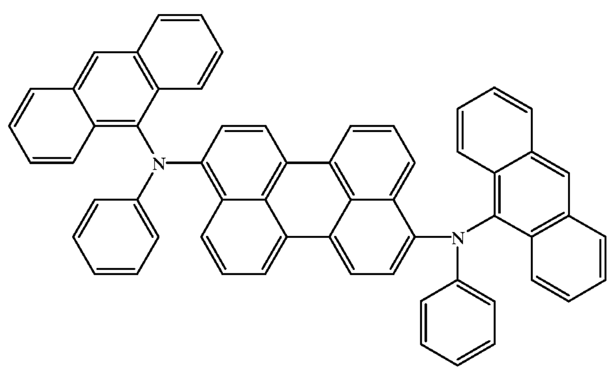 |
| (28) | 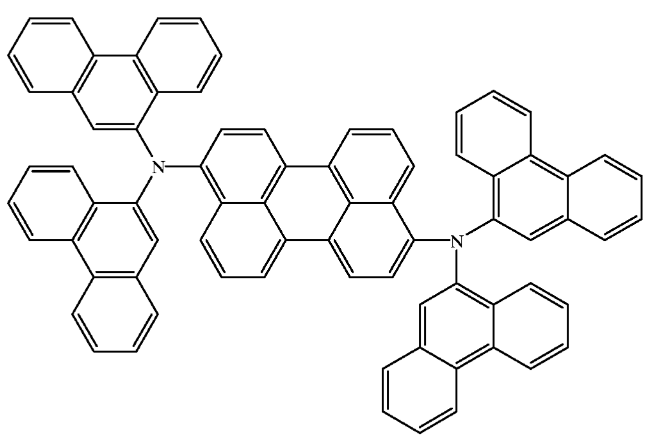 |

TABLE 1-continued
| Compound | Chemical structure |
|---|---|
| (29) | 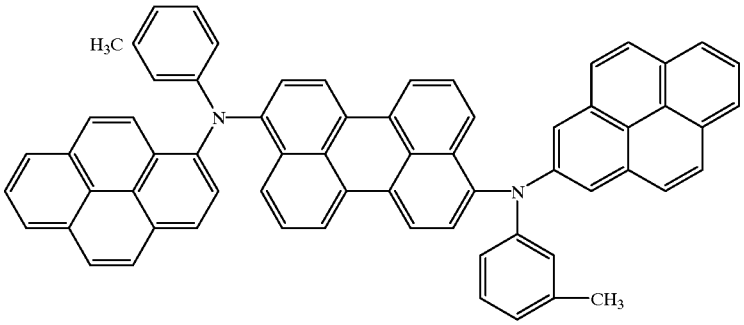 |
| (30) | 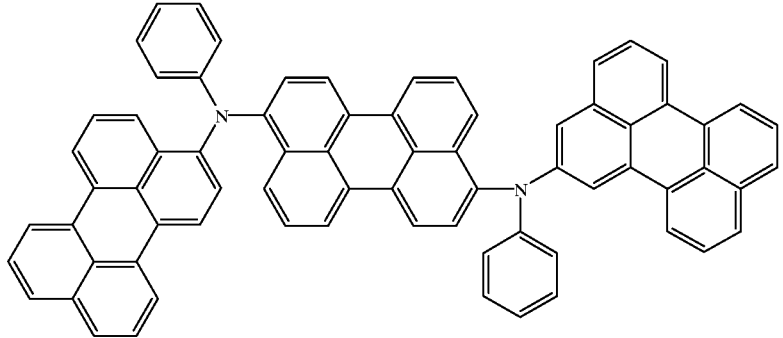 |
| (31) | 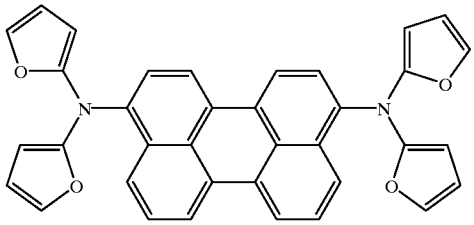 |
| (32) | 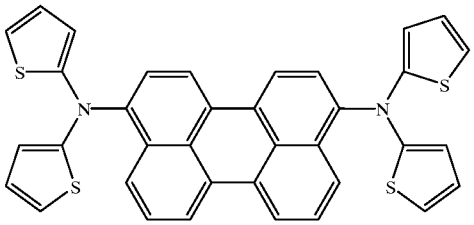 |

TABLE 1-continued
| Compound | Chemical structure |
|---|---|
| (33) | 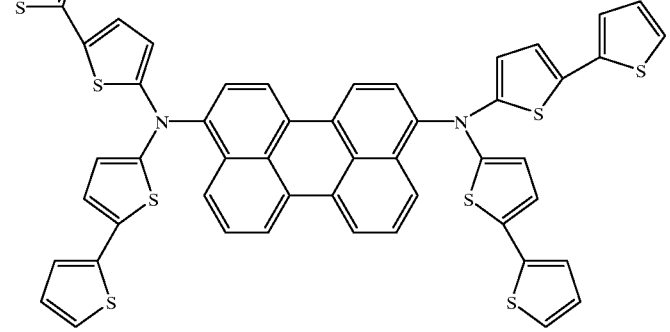 |
| (34) | 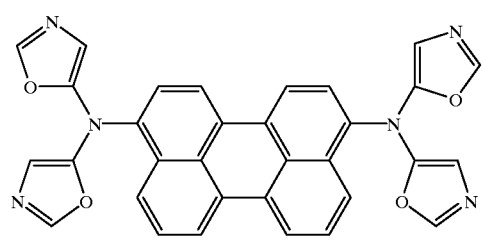 |
| (35) | 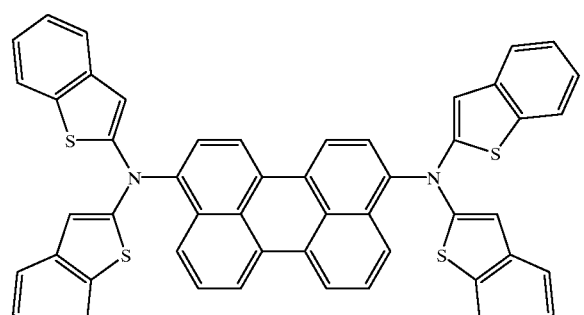 |
| (36) | 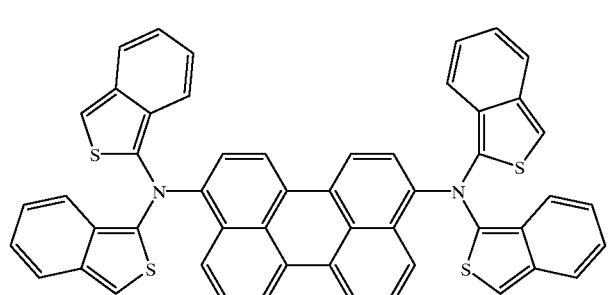 |

TABLE 1-continued

| Compound | Chemical structure |
|---|---|
| (37) | 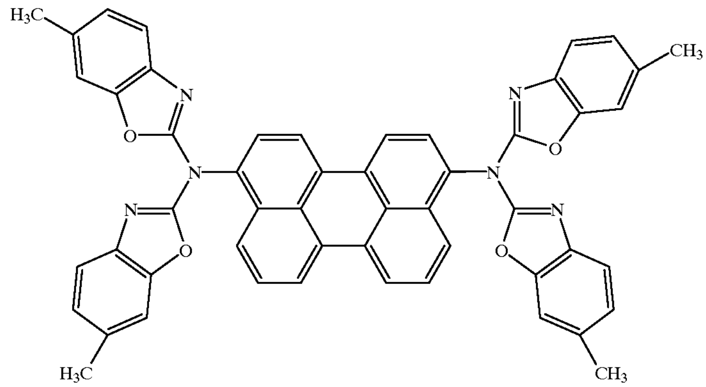 |
| (38) | 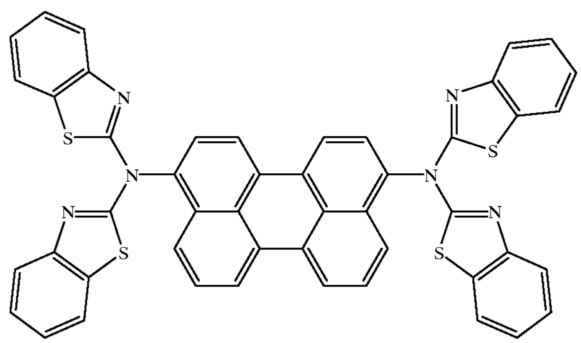 |
| (39) | 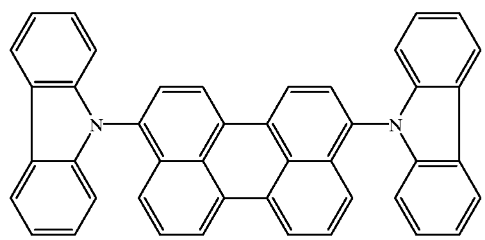 |
| (40) | 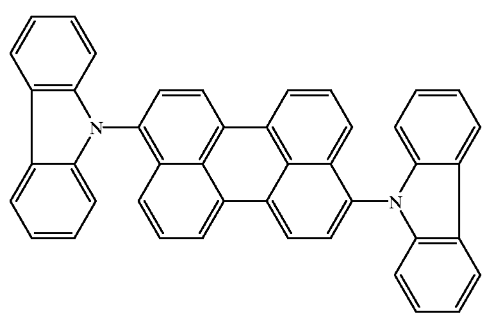 |
| (41) | 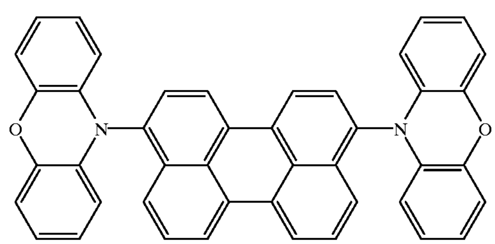 |

TABLE 1-continued

| Compound | Chemical structure |
| --- | --- |
| (42) | 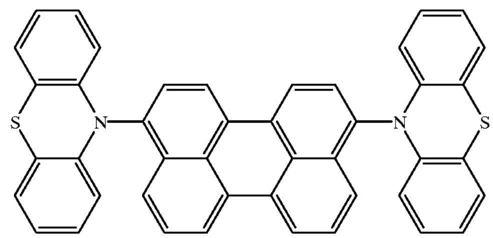 |
| (43) | 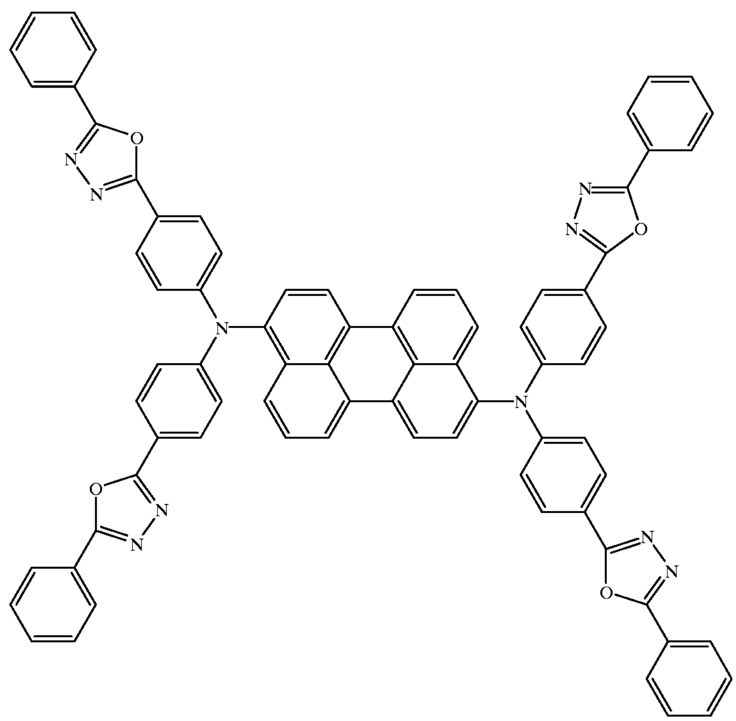 |
| (44) | 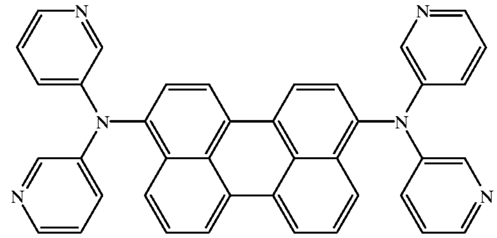 |

TABLE 1-continued

| Compound | Chemical structure |
|---|---|
| (45) | 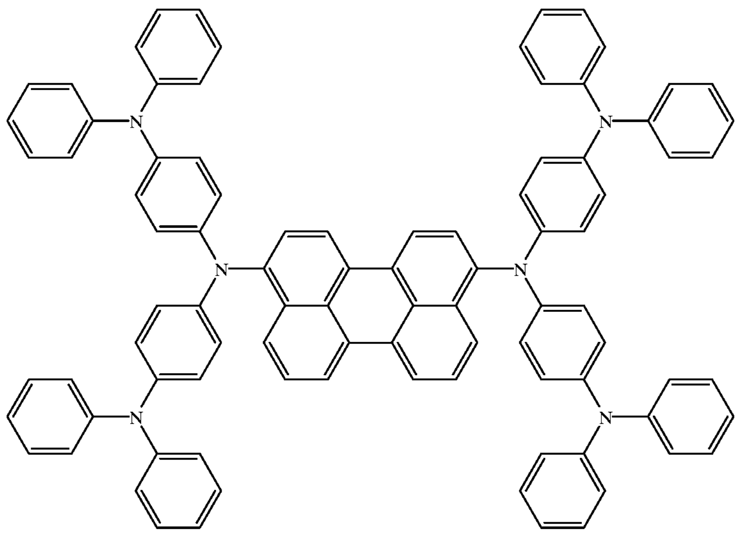 |
| (46) | 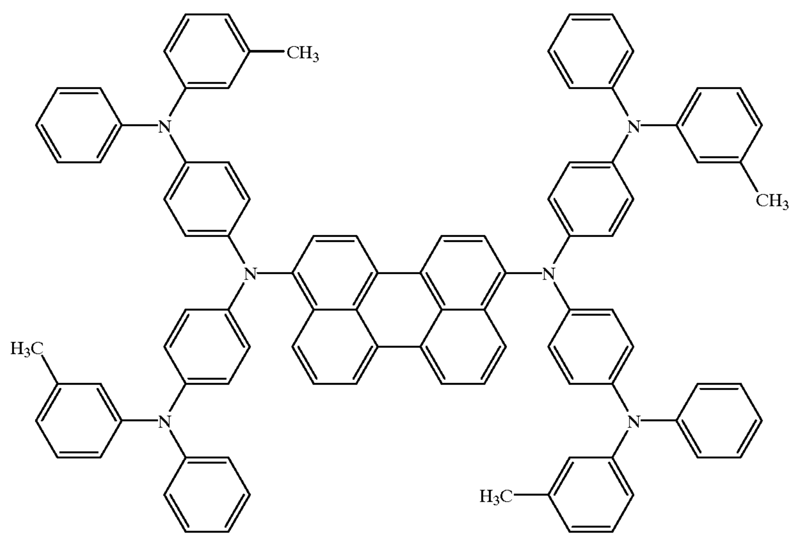 |

TABLE 1-continued
| Compound | Chemical structure |
|---|---|
| (47) | 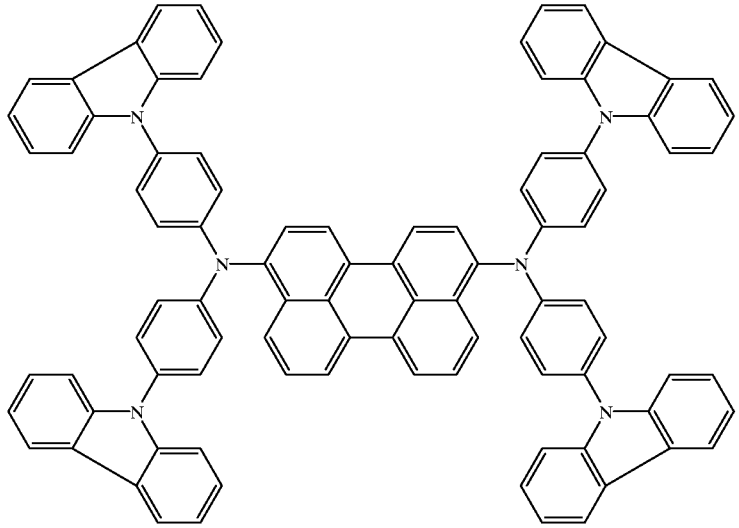 |
| (48) | 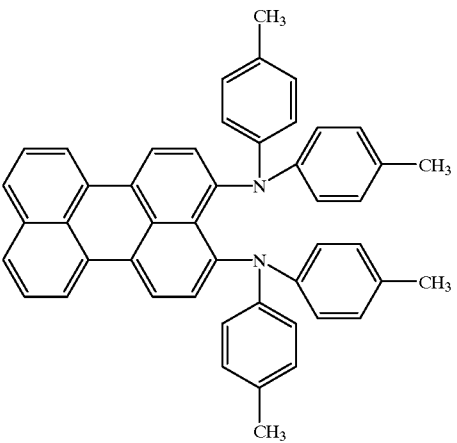 |
| (49) | 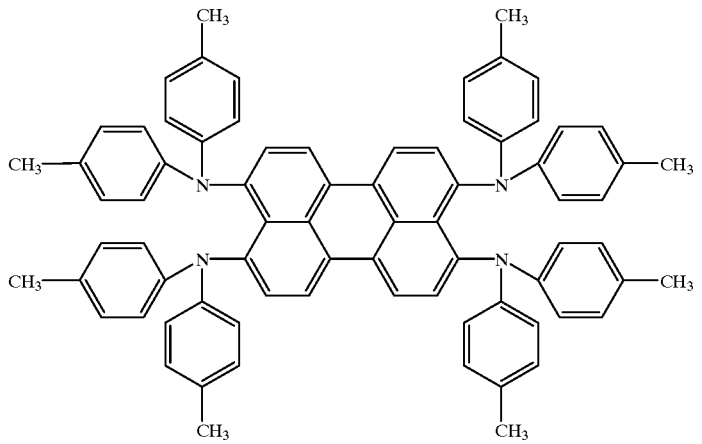 |

TABLE 1-continued
| Compound | Chemical structure |
| --- | --- |
| (50) | 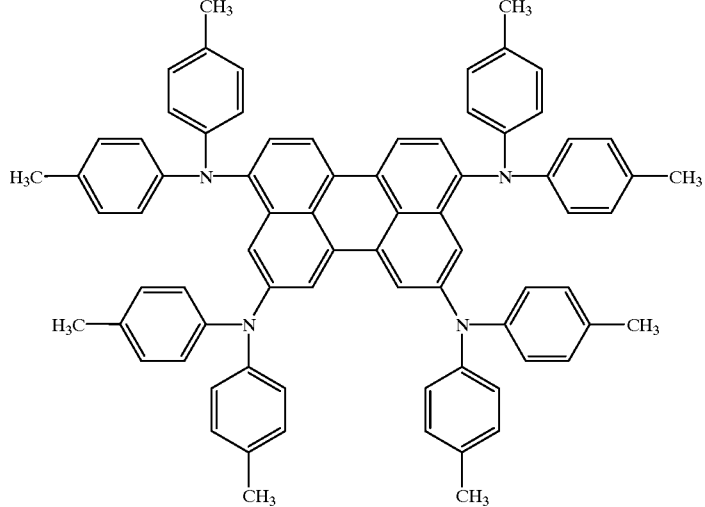 |
| (51) | 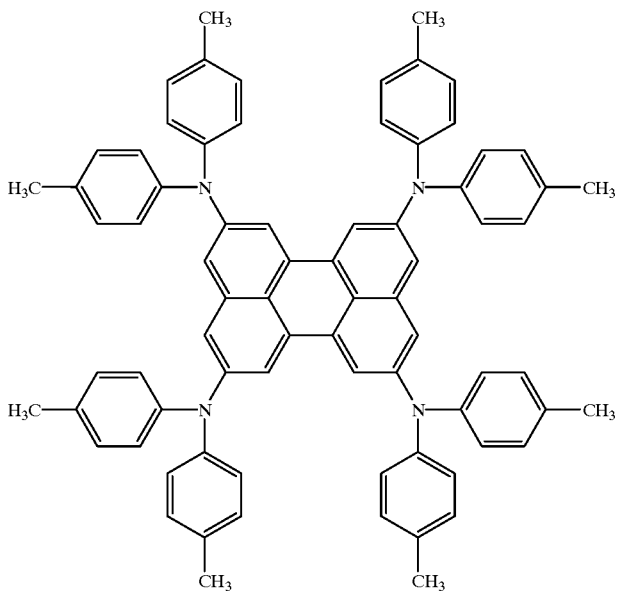 |
| (52) | 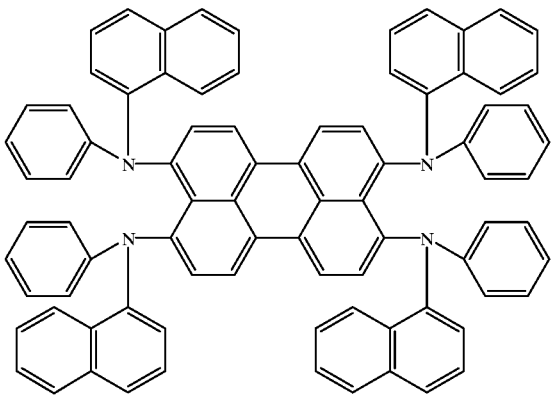 |

TABLE 1-continued
| Compound | Chemical structure |
|---|---|
| (53) | 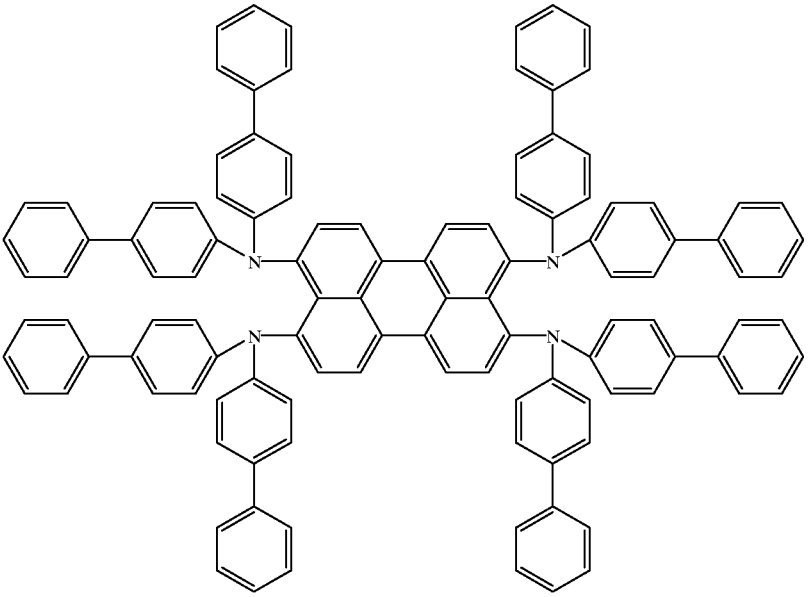 |
| (54) | 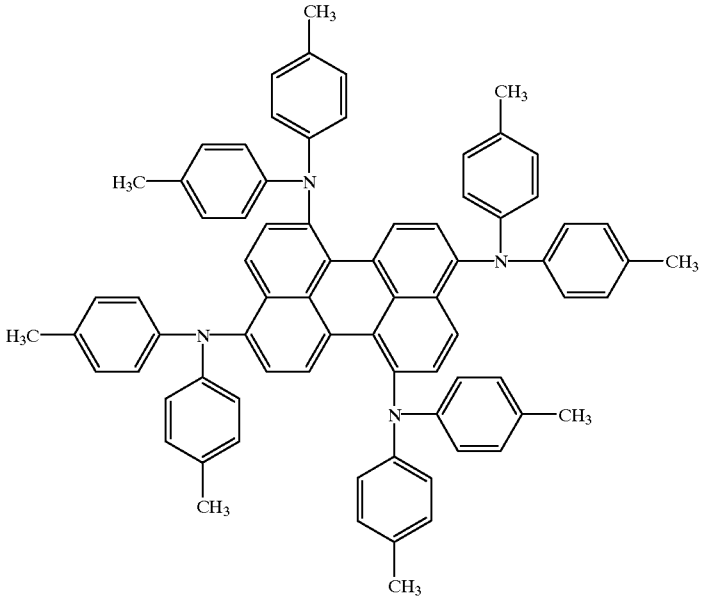 |

TABLE 1-continued

| Compound | Chemical structure |
|---|---|
| (55) | 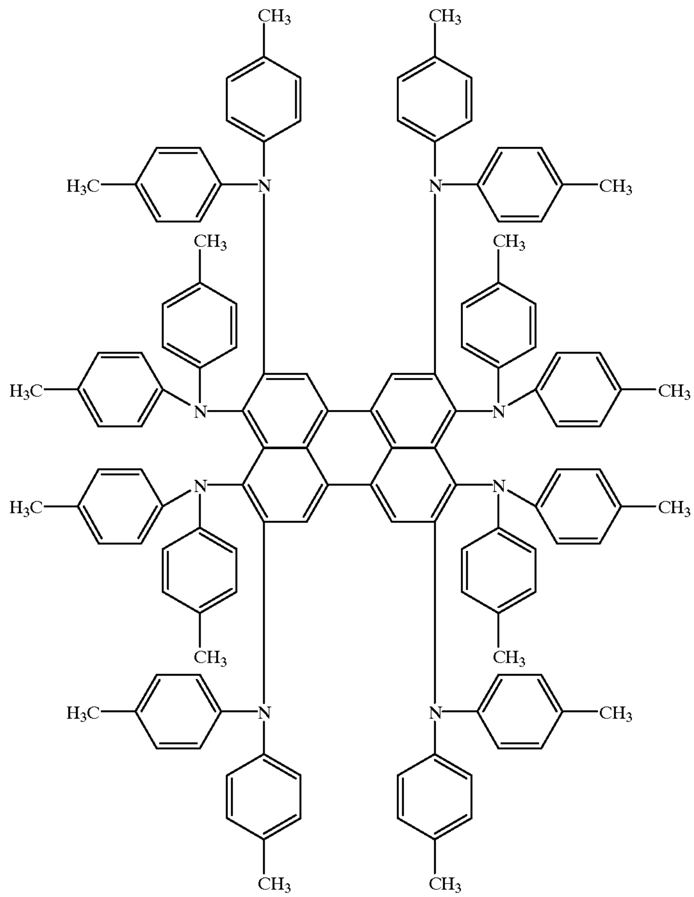 |

TABLE 1-continued
| Compound | Chemical structure |
| --- | --- |
| (56) | 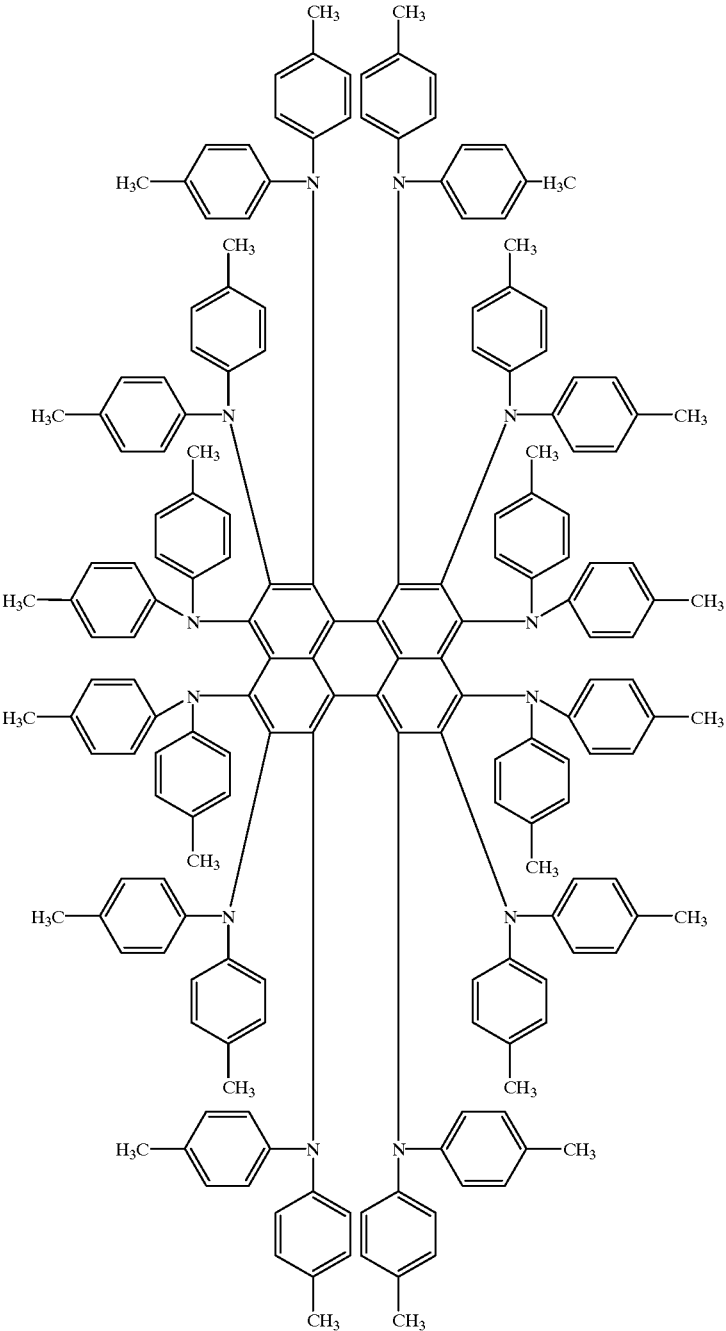 |

TABLE 1-continued

| Compound | Chemical structure |
|---|---|
| (57) | *(hexakis(di-p-tolylamino)triphenylene structure)* |

TABLE 1-continued
| Compound | Chemical structure |
| --- | --- |
| (58) | 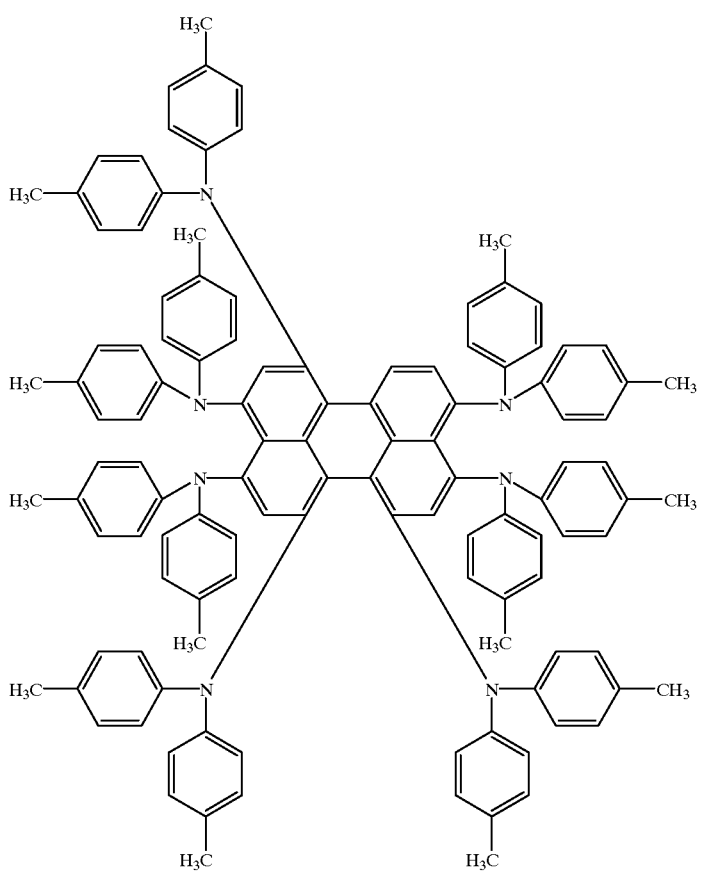 |

TABLE 1-continued
| Compound | Chemical structure |
| --- | --- |
| (59) | 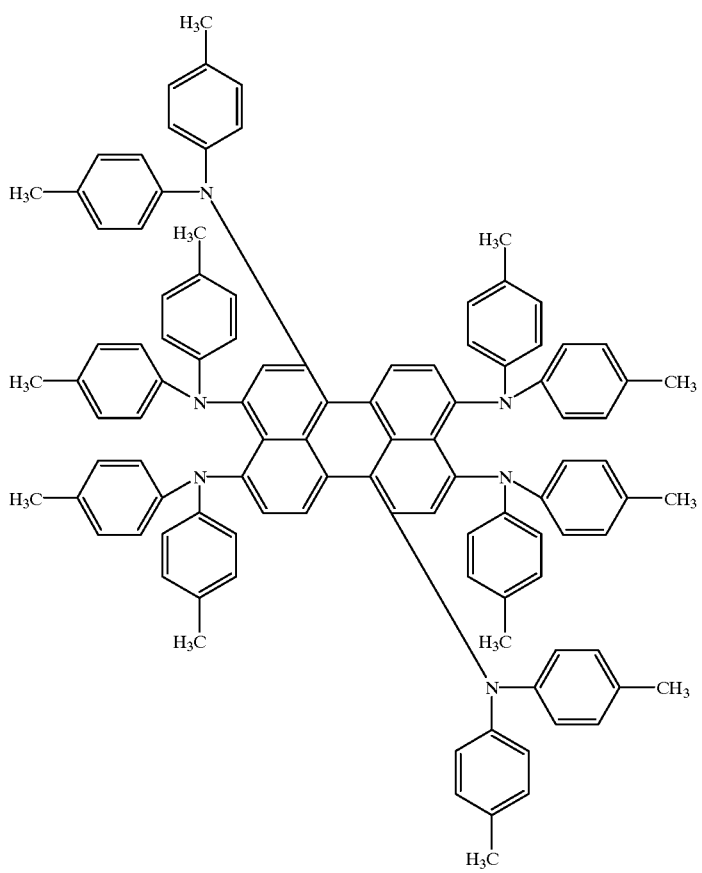 |
| (60) | 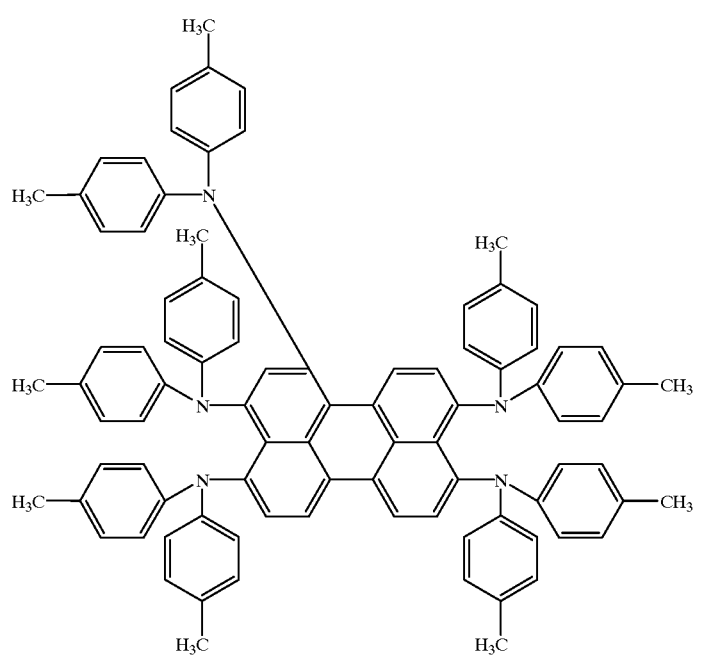 |

TABLE 1-continued
| Compound | Chemical structure |
|---|---|
| (61) | 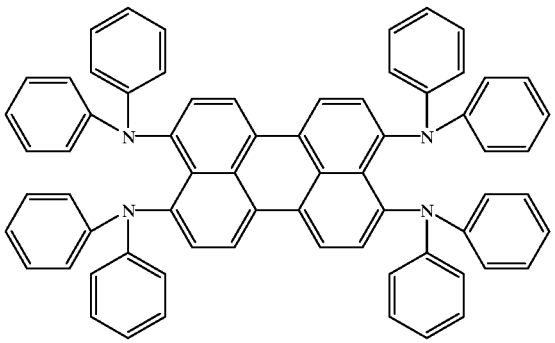 |
| (62) | 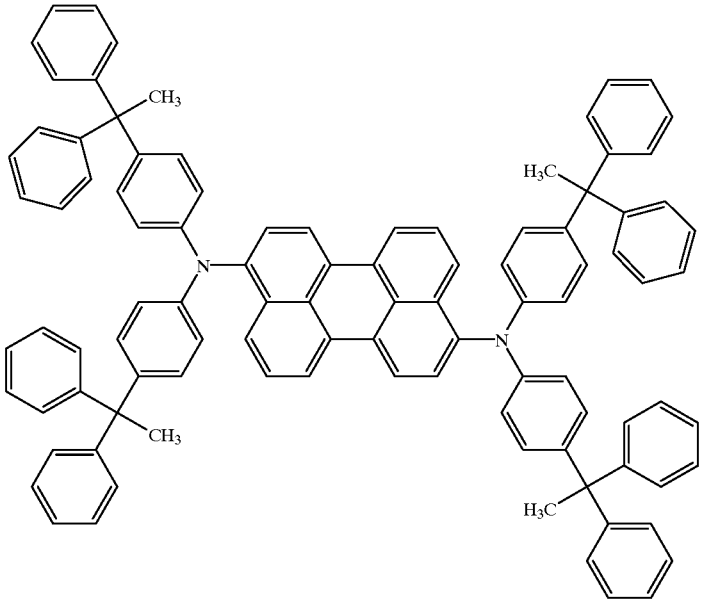 |

TABLE 1-continued

| Compound | Chemical structure |
| --- | --- |
| (63) | 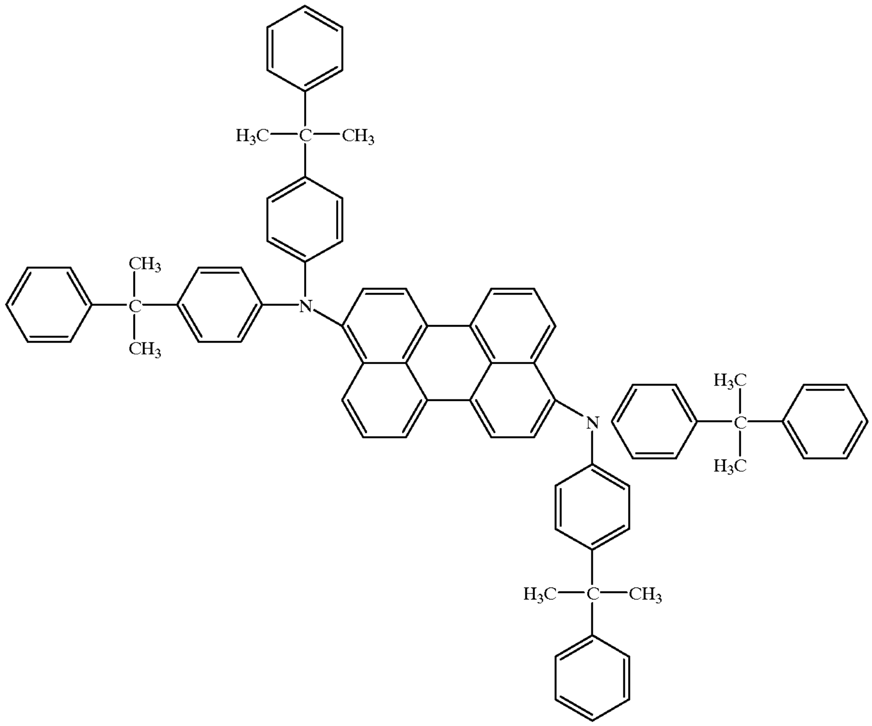 |
| (64) | 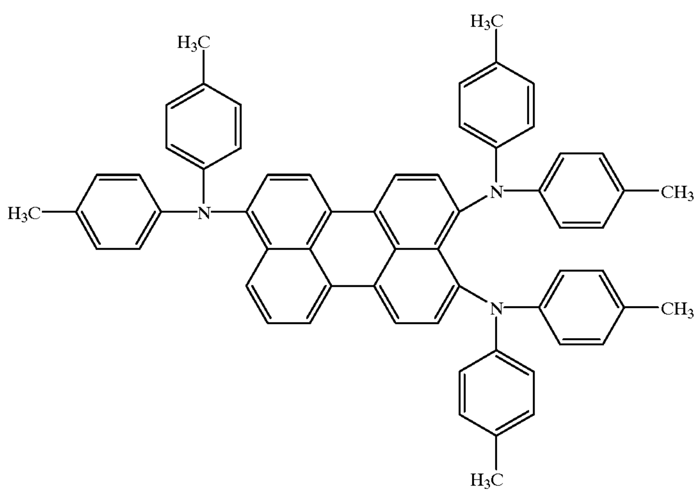 |

TABLE 1-continued
| Compound | Chemical structure |
| --- | --- |
| (65) | 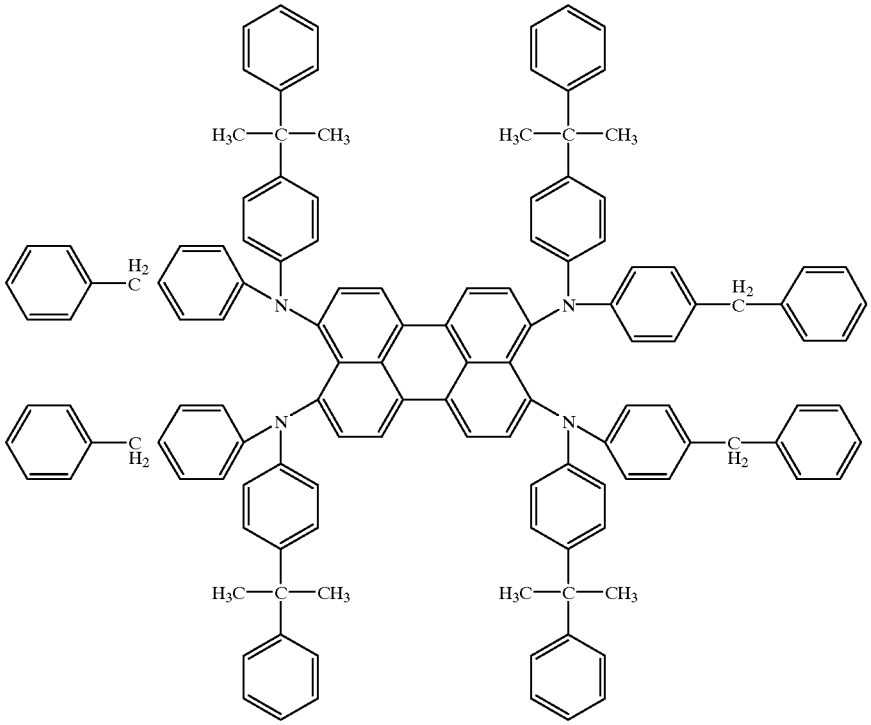 |
| (66) | 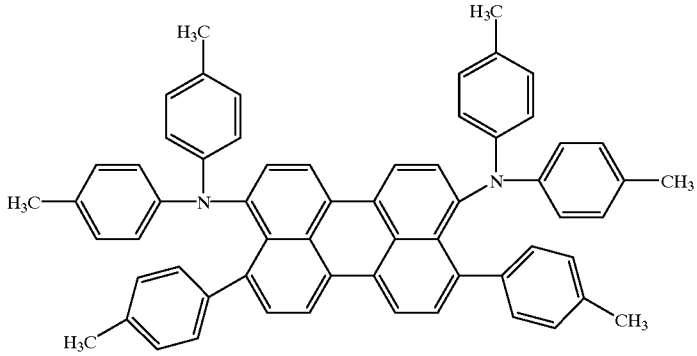 |
| (67) | 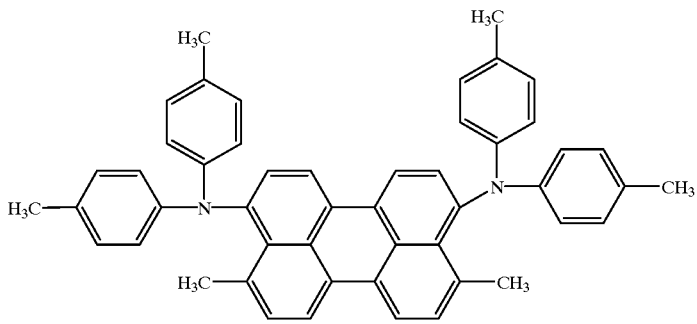 |

TABLE 1-continued

| Compound | Chemical structure |
|---|---|
| (68) | 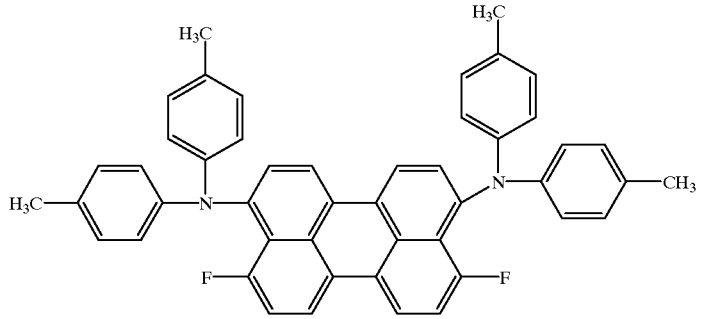 |

In the compound of the formula [3], each of $Q^1$ and $Q^2$ is independently a substituted or non-substituted hydroxyquinoline derivative or a substituted or non-substituted hydroxybenzoquinoline derivative. Specific examples of the substituents are the same as those of the formula [1] or [2].

L is a halogen atom, a substituted or non-substituted alkyl group, a substituted or non-substituted cycloalkyl group, a substituted or non-substituted aryl group, a substituted or non-substituted aromatic heterocyclic group, or a ligand of —OR in which R is a hydrogen atom, a substituted or non-substituted alkyl group, a substituted or non-substituted cycloalkyl group, a substituted or non-substituted aryl group or a substituted or non-substituted aromatic heterocyclic group or —O—Ga—$Q^3(Q^4)$ in which $Q^3$ and $Q^4$ have the same meanings as those of $Q^1$ and $Q^2$.

Specific examples of the halogen atom, the substituted or non-substituted alkyl group, the substituted or non-substituted aryl group and the substituted or non-substituted aromatic heterocyclic group included in the definition of L or R are the same as those explained with regard to the formula [1] or [2].

Further, examples of the substituted or non-substituted cycloalkyl group include cyclopentyl, cyclohexyl, cycloheptyl, cyclononyl and cyclodecanyl.

Although not specially limited, specific examples of the compound of the formula [3] include bis(2-methyl-8-hydroxyquinolinato)(1-naphtholato) gallium complex, bis (2-methyl-8-hydroxyquinolinato)(2-naphtholato) gallium complex, gallium bis(2-methyl-8-hydroxyquinolinato) (phenolato) gallium complex, bis(2-methyl-8-hydroxyquinolinato)(4-cyano-1-naphthaolato) gallium complex, bis(2,4-dimethyl-8-hydroxyquinolinato)(1-naphtholato) gallium complex, bis(2,5-dimethyl-8-hydroxyquinolinato)(2-naphtholato) gallium complex, bis (2methyl-5-phenyl-8-hydroxyquinolinato)(phenolato) gallium complex, bis(2-methyl-5-cyano-8-hydroxyquinolinato)(4-cyano-1-naphtolato) gallium complex, bis(2-methyl-8-hydroxyquinolinato) chlorogallium complex, and bis(2-methyl-8-hydroxyquinolinato)(o-cresolato) gallium complex.

The method of synthesizing the compound of the formula [3] and other specific examples thereof are disclosed in JP-A-10-88121.

An organic EL device is a device having a structure in which a mono- or multi-layered organic thin layer is formed between an anode and a cathode. In a mono-layered device, a light-emitting layer is formed between the anode and the cathode. The light-emitting layer contains a light-emitting material, and in addition thereto, it may contain a hole-injecting material for transporting holes injected from the anode to the light-emitting material, or an electron-injecting material for transporting electrons injected from the cathode to the light-emitting material. The multi-layered organic EL device has one of laminated-layer structures, for example, (anode/hole-injecting layer/light-emitting layer/(athode), (anode/light-emitting layer/electron-injecting layer/cathode) and (anode/hole-injecting layer/light-emitting layer/electron-injecting layer/cathode). The compound of the formula [1] provided by the present invention has intense fluorescence of red and exhibits excellent light emission by an electric field when it is in a solid state, and it can be therefore used as a light-emitting material. Further, when the compound of the formula [1] is doped in an optimum ratio in a light-emitting layer, a high light emission efficiency and an optimum light emission wavelength can be selected. The content of the compound of the formula [1] based on a host material in the light-emitting layer is preferably in the range of 0.001% by weight to 50% by weight, further effectively in the range of from 0.01% by weight to 10% by weight.

Each of the above hole-injecting layer, light-emitting layer and electron-injecting layer may be formed of two or more layers.

The host material that can be used in the light-emitting layer together with the compound of the formula [1] includes electron-injecting materials such as quinoline metal complex, benzoquinoline metal complex, benzoxazole metal complex, benzothiazole metal complex, benzoimidazole metal complex, benzotriazole metal complex, an imidazole derivative, an oxadiazole derivative, thiadiazole derivative and a triazole derivative, hole-injecting materials such as a stilbene derivative, a butadiene derivative, benzidine type triphenylamine derivative, a styrylamine type triphenylamine derivative, a diaminoanthracene type triphenylamine derivative and diaminophenanthrene type triphenylamine derivative, and electrically conductive polymers such as polyvinyl carbazole and polysilane.

The light-emitting material or the dopant that can be used together with the compound of the formula [1] includes anthracene, naphthalene, phenanthrene, pyrene, tetracene, coronene, chrysene, fluorescein, perylene, phthaloperylene, naphthaloperylene, perinone, phthaoperinone, naphthaloperinone, diphenylbutadiene, tetraphenylbutadiene, coumarine, oxadiazole, aldazine, bisbenzoxazoline, bisstyryl, pyrazine, cyclopentadiene, quinoline metal complex, aminoquinoline metal complex, benzoquinoline metal complex, imine, diphenylethylene, vinyl anthracene, diaminocarbazole, pyran, thiopyran, polymethine, merocyanine, an imidazole-chelated oxynoid compound, quinacridone, rubrene, and derivatives of these.

The light-emitting layer may contain a hole-injecting material or an electron-injecting material as required in addition to the light-emitting material and the dopant.

The hole-injecting material is selected from compounds which are capable of injecting holes, have an excellent effect of injecting holes to a light-emitting layer or a light-emitting material, prevent the movement of excitons generated in a light-emitting layer to an electron-injecting layer or an electron-injecting material and have excellent thin film formability. Specific examples of the hole-injecting material include a phthalocyanine derivative, a naphthalocyanine derivative, a porphyrin derivative, triazole, imidazole, imidazolone, imidazolthione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives of these, polyvinylcarbazole, polysilane and an electrically conductive polymer. However, the hole-transporting material shall not be limited to the above materials.

In the organic EL device of the present invention, the hole-injecting material which is more effective is an aromatic tertiary amine derivative or a phthalocyanine derivative. Although not specially limited, specific examples of the tertiary amine derivative include triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl)-1,1'-biphenyl-4,4'-diamine, N,N'-(methylphenyl)-N,N'-di(4-n-butylphenyl)-phenanthrene-9,10-diamine, N,N-bis(4-di-4-tolylaminophenyl)-4-phenylcyclohexane, and origomers or polymers having aromatic tertiary amine structures of these. Although no specially limited, specific examples of the phthalocyanine (Pc) derivative include phthalocyanine derivatives or naphthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, and GaPc—O—GaPc.

The electron-injecting material is a material which is capable of injecting electrons, has the excellent effect of injecting electrons into a light-emitting layer or light-emitting material, prevents excitons generated in the light-emitting layer from moving into a hole-injecting zone and has excellent thin film formability. Although not specially limited, examples of the electron-injecting material include quinoline metal complex, oxadiazole, benzothiazole metal complex, benzoxazole metal complex, benzoimidazole metal complex, fluorenone, anthraquinodimethane, diphenoquinone, thiopyran dioxide, oxadiazole, thiaziazole, tetrazole, perylenetetracarboxylic acid, fluorenylidenemethane, anthraquinodimethane, anthrone and derivatives of these. The hole-injecting material may be sensitivity-increased by incorporating an electron-receiving material, and the electron-injecting material may be sensitivity-increased by incorporating an electron-donating material.

In the organic EL device of the present invention, metal complex compounds or nitrogen-containing five-membered ring derivatives are more effective electron-injecting materials. Of these, the compound of the formula [3] is preferred.

In addition to the compound of the formula [3], specific examples of the metal complex compounds include lithium 8-hydroxyquinolinate, zinc bis(8-hydroxyquinolinate), copper bis(8-hydroxyquinolinate), manganese bis(8-hydroxyquinolinate), aluminum tris(8-hydroxyquinolinate), aluminum tris(2-methyl-8-hydroxyquinolinate), gallium tris (8-hydroxyquinolinate), beryllium bis(10-hydroxybenzo[h] quinolinate) and zinc bis(10-hydroxybenzo[h]quinolinate), although the metal complex compounds shall not be limited to these.

As a nitrogen-containing five-membered derivative an oxazole, thiazole, thiadiazole, or triazole derivative is preferred. Although not specially limited, specific examples of the nitrogen-containing five-membered derivative include 2,5-bis(1-phenyl)-1,3,4-oxazole, dimethylPOPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole and 1,4-bis[2-(5-phenyltriazolyl)]benzene.

The electrically conductive material used for the anode of the organic EL device is suitably selected from those materials having a work function of greater than 4 eV. The electrically conductive material includes carbon, aluminum, vanadium, iron, cobalt, nickel, tungsten, silver, gold, platinum, palladium, alloys of these, metal oxides such as tin oxide and indium oxide used for ITO substrates or NESA substrates, and organic electrically conductive polymers such as polythiophene and polypyrrole.

The electrically conductive material used for the cathode is suitably selected from those having a work function of smaller than 4 eV. The electrically conductive material includes magnesium, calcium, tin, lead, titanium, yttrium, lithium, lithium fluoride, ruthenium, manganese and alloys of these. Examples of the alloys include magnesium/silver, magnesium/indium and lithium/aluminum, while the electrically conductive material shall not be limited to these. The ratio of components of the alloy is controlled depending upon a heating temperature, an atmosphere and a vacuum degree, and a proper ratio is selected. Each of the anode and the cathode may have a layer structure formed of two layers or more as required.

For the effective light emission of the organic EL device, at least one of the electrodes is desirably sufficiently transparent in the light emission wavelength region. Further, the substrate is desirably transparent as well. The transparent electrode is produced from the above electrically conductive material by a deposition method or a sputtering method such that a predetermined light transmittance is secured. The electrode on the light emission surface side preferably has a light transmittance of at least 10%.

The substrate is not specially limited so long as it has adequate mechanical and thermal strength and has transparency. For example, it is selected from glass substrates and substrates of transparent polymers such as a polyethylene substrate, a polyethylene substrate, a polyether sulfone substrate and a polypropylene substrate.

When the organic EL device is formed of a multi-layered structure, a decrease in the brightness and the lifetime caused by quenching can be prevented. Further, at least two kinds of light-emitting materials, at least two kinds of doping materials, at least hole-injecting materials for injecting carriers, and at least two kinds of electron-injecting materials may be used in combination each as required. Further, each of the hole-injecting layer, the light-emitting layer and the electron-injecting layer may be formed of two layers or more, a device structure is selected such that holes or electrons are efficiently injected from the electrodes and transported in layers.

In the organic EL device of the present invention, each layer can be formed by any one of dry film forming methods such as a vacuum deposition method, a sputtering method, a plasma method and an ion plating method and wet film forming methods such as a spin coating method, a dipping method and a flow coating method. The thickness of each layer is not specially limited, while each layer is required to have a proper thickness. When the layer thickness is too large, inefficiently, a high voltage is required to achieve predetermined emission of light. When the layer thickness is too small, the layer is liable to have a pinhole, etc., so that sufficient light emission brightness is hard to obtain when an electric field is applied. Generally, the thickness of each layer is preferably in the range of from 1 nm to 10 $\mu$m, more preferably 10 nm to 0.2 $\mu$m.

In the wet film forming method, material(s) for forming an intended layer is dissolved or dispersed in a proper solvent such as chloroform, tetrahydrofuran or dioxane, and a thin film is formed from the solution or dispersion. The solvent shall not be limited to the above solvents. For improving the film formability and preventing the occurrence of pinholes in any layer, the above solution or dispersion for forming the layer may contain a proper polymer and a proper additive.

The above polymer includes insulating resins such as polystyrene, polycarbonate, polyarylate, polyester, polyamide, polyurethane, polysulfone, polymethyl methacrylate, polymethyl acrylate and cellulose, photoconductive polymers such as poly-N-vinylcarbozole and polysilane, and electrically conductive polymers such as polythiophene and polypyrrole. The above additive includes an antioxidant, an ultraviolet absorbent and a plasticizer.

In the organic EL device of the present invention, the light-emitting layer may contain, in addition to the compound of the formula [1], at least one of a light-emitting material, a doping material, a hole-injecting material and an electron-injecting material. For improving the organic EL device of the present invention in the stability against temperature, humidity and ambient atmosphere, a protective layer may be formed on the surface of the device, or the device as a whole may be sealed with a silicone oil, or the like.

When the compound of the present invention is used in a light-emitting layer of an organic EL device, and further, when the light-emitting layer is combined with the specified hole-injecting layer or the electron-injecting layer, the organic EL device can be improved in organic EL device characteristics such as light emission efficiency and maximum light emission brightness. Further, the organic EL device of the present invention is remarkably stable against heat and electric current and gives a practically usable light emission brightness at a low driving voltage, so that the deterioration which is a big problem of conventional devices can be remarkably decreased.

The organic EL device of the present invention has significant industrial values since it can be adapted for a flat panel display of an on-wall television set, a flat light-emitting device, a light source for a copying machine or a printer, a light source for a liquid crystal display or a meter, a display signboard and a signal light.

EXAMPLES

The present invention will be explained more in detail with reference to Examples hereinafter.
Synthesis of Compound (1)

5 g of 3,10-diaminoperylene, 45 g of 4-methyl-iodobenzene, 28 g of sodium hydroxide and 0.5 g of copper (I) chloride were added to 20 ml of nitrobenzene, and the mixture was stirred under heat at 200° C. for 50 hours. Then, the mixture was diluted with 500 ml of water and extracted with ethyl acetate, and the extract was concentrated and purified by silica gel column chromatography to give 3 g of a powder having red fluorescence. The powder was analyzed by FD-MS for a molecular weight and for NMR spectrum to show that the powder was Compound (1).
Synthesis of Compound (2)

6.5 g of 3,9-dibromoperylene, 16.2 g of p,p'-ditolylamine, 12 g of potassium carbonate and 0.5 g of a copper powder were added to 50 ml of 1,3-dimethyl-2-imidazolidinon, and the mixture was stirred under heat at 200° C. for 50 hours. Then, the mixture was diluted with 500 ml of water and extracted with ethyl acetate, and the extract was concentrated and purified by silica gel column chromatography to give 12 g of a powder having red fluorescence. The powder was analyzed by FD-MS for a molecular weight and for NMR spectrum to show that the powder was Compound (2). FIG. 1 shows the infrared absorption spectrum (KBr tablet method) of Compound (2).
Synthesis of Compound (24)

5.5 g of 3,10-dibromoperylene, 12.2 g of 2-naphthyl-phenylamine, 8 g of potassium carbonate and 0.5 g of a copper powder were added to 50 ml of 1,3-dimethyl-2-imidazolidinon, and the mixture was stirred under heat at 200° C. for 50 hours. Then, the mixture was diluted with 500 ml of water and extracted with ethyl acetate, and the extract was concentrated and purified by silica gel column chromatography to give 13 g of a powder having orange fluorescence. The powder was analyzed by FD-MS for a molecular weight and for NMR spectrum to show that the powder was Compound (24).
Synthesis of Compound (49)

Figure 2:
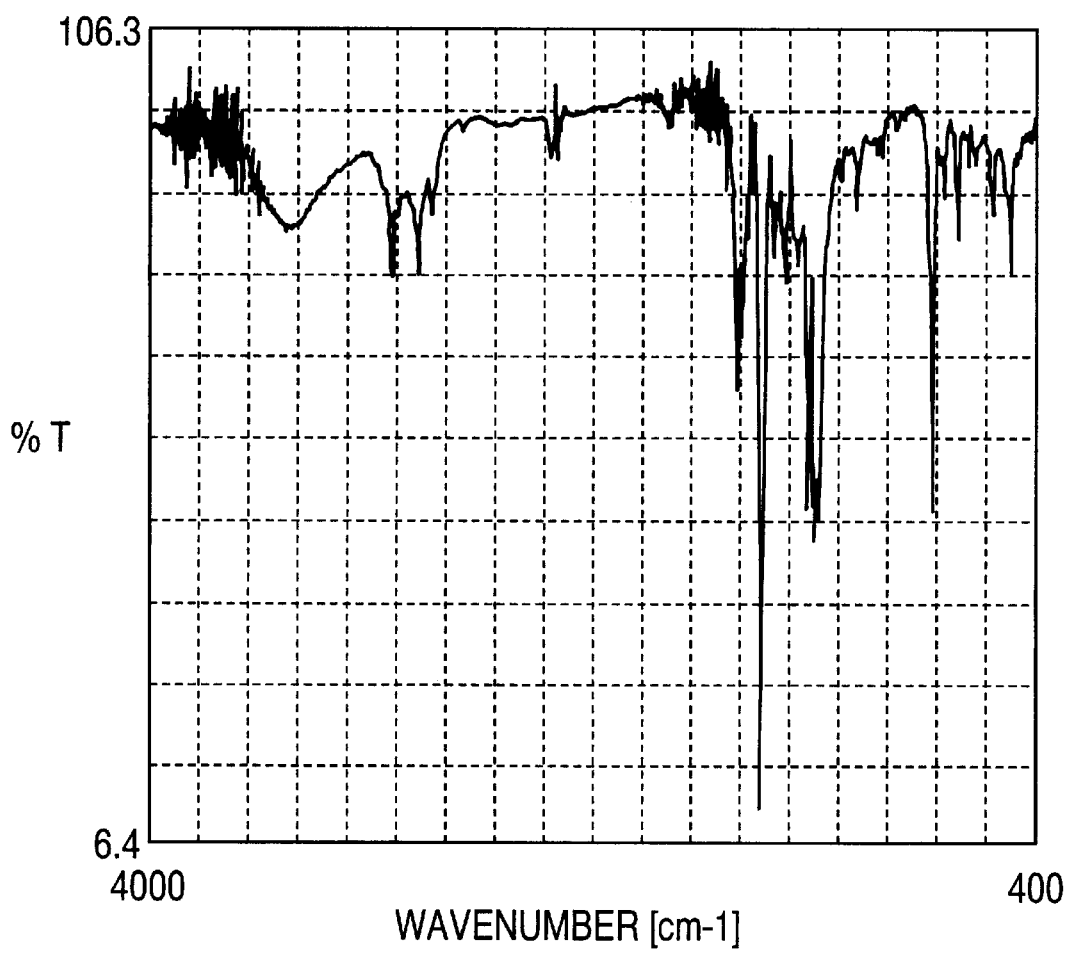
FIG. 2 shows an infrared absorption spectrum (KBr tablet method) of Compound (49).

10.5 g of 3,4,9,10-tetrabromoperylene, 36.2 g of p,p'-ditolylamine, 16 g of potassium carbonate and 1.0 g of a copper powder were added to 100 ml of 1,3-dimethyl-2-imidazolidinon, and the mixture was stirred under heat at 200° C. for 50 hours. Then, the mixture was diluted with 500 ml of water and extracted with ethyl acetate, and the extract was concentrated and purified by silica gel column chromatography to give 8 g of a powder having red fluorescence. The powder was analyzed by FD-MS for a molecular weight and for NMR spectrum to show that the powder was Compound (49). FIG. 2 shows the infrared absorption spectrum (KBr tablet method) of Compound (49).

Examples using the compound of the present invention will be shown hereinafter. In Examples, the properties of organic EL devices having an electrode area of 2 mm×2 mm were measured.

Example 1

Compound (53) was dissolved in methylene chloride, and the solution was spin-coated on a cleaned glass substrate with an ITO electrode to form a hole-injecting type light-emitting layer having a thickness of 50 nm. Then, gallium bis(2-methyl-8-hydroxyquinolinate)(1-naphtolate) complex was vacuum-deposited to form an electron-injecting layer having a thickness of 40 nm, and an electrode having a thickness of 100 nm was formed thereon from a magnesium/silver alloy having a magnesium/silver mixing weight ratio of 10/1, to obtain an organic EL device. The light-emitting layer and the electron-injecting layer were formed by deposition under a vacuum of $10^{-6}$ Torr at a substrate temperature of room temperature. The device showed a red light emission having a light emission brightness of 150 (cd/m$^2$) at a direct current voltage of 5 V, a maximum light emission brightness of 2,200 (cd/m$^2$) and a light emission efficiency of 0.40 (1 m/W).

Example 2

4,4'-bis[N-(1-naphthyl)-N-phenylamino]biphenyl(α-NPD) was vacuum-deposited on a cleaned glass substrate with an ITO electrode to form a hole-injecting layer having a thickness of 30 m. Then, Compound (49) as a light-emitting material was vacuum-deposited to form a light-emitting layer having a thickness of 30 nm. Further, gallium bis(2-methyl-8-hydroxyquinolinate)(phenolate) complex was vacuum-deposited to form an electron-injecting layer having a thickness of 30 nm. An electrode having a thickness of 100 nm was formed thereon from a magnesium/silver alloy having a magnesium/silver mixing weight ratio of 10/1, to obtain an organic EL device. The hole-injecting layer and the light-emitting layer were formed by deposition under a vacuum of $10^{-6}$ Torr at a substrate temperature of room temperature. The device showed a red light emission having a light emission brightness of 200 (cd/m$^2$) at a direct current voltage of 5 V, a maximum light emission brightness of 5,000 (cd/m$^2$) and a light emission efficiency of 0.8 (1 m/W).

Example 3

4,4',4"-tris(N-(3-methylphenyl)-N-phenylamino)triphenylamine was vacuum-deposited on a cleaned glass substrate with an ITO electrode to form a hole-injecting layer having a thickness of 40 nm. Then, α-NPD was vacuum-deposited to form a second hole-injecting layer having a thickness of 10 nm. Further, Compound (61) was vacuum-deposited to form a light-emitting layer having a thickness of 30 nm. Further, gallium bis(2-methyl-8-hydroxyquinolinate)(1-phenolate) complex was vacuum-deposited to form an electron-injecting layer having a thickness of 30 nm. An electrode having a thickness of 150 nm was formed thereon from an aluminum/lithium alloy having an aluminum/lithium mixing weight ratio of 25/1, to obtain an organic EL device. The hole-injecting layers and the light-emitting layer were formed by deposition under a vacuum of $10^{-6}$ Torr at a substrate temperature of room temperature. The device showed a red light emission having a light emission brightness of 210 (cd/m$^2$) at a direct current voltage of 5 V, a maximum light emission brightness of 4,000 (cd/m$^2$) and a light emission efficiency of 0.6 (1 m/W).

Example 4

4,4'-bis[N-(1-naphthyl)-N-phenylamino]biphenyl (α-NPD) was vacuum-deposited on a cleaned glass substrate with an ITO electrode to form a hole-injecting layer having a thickness of 30 m. Then, Compound (65) as a light-emitting material was vacuum-deposited to form a light-emitting layer having a thickness of 30 nm. Further, tris(8-hydroxyquinolinate)aluminum complex was vacuum-deposited to form an electron-injecting layer having a thickness of 30 nm. An electrode having a thickness of 100 nm was formed thereon from a magnesium/silver alloy having a magnesium/silver mixing weight ratio of 10/1, to obtain an organic EL device. The hole-injecting layer and the light-emitting layer were formed by deposition under a vacuum of $10^{-6}$ Torr at a substrate temperature of room temperature. The device showed a red light emission having a light emission brightness of 150 (cd/m$^2$) at a direct current voltage of 5 V, a maximum light emission brightness of 4,000 (cd/m$^2$) and a light emission efficiency of 0.6 (1 m/W).

Example 5

4,4',4"-tris(N-(3-methylphenyl)-N-phenylamino)triphenylamine was vacuum-deposited on a cleaned glass substrate with an ITO electrode to form a hole-injecting layer having a thickness of 40 nm. Then, α-NPD was vacuum-deposited to form a second hole-injecting layer having a thickness of 10 nm. Further, Compound (53) was vacuum-deposited to form a light-emitting layer having a thickness of 30 nm. Further, gallium bis(2-methyl-8-hydroxyquinolinate)(1-phenolate) complex was vacuum-deposited to form an electron-injecting layer having a thickness of 30 nm. An electrode having a thickness of 150 nm was formed thereon from an aluminum/lithium alloy having an aluminum/lithium mixing weight ratio of 25/1, to obtain an organic EL device. The hole-injecting layers and the light-emitting layer were formed by deposition under a vacuum of $10^{-6}$ Torr at a substrate temperature of room temperature. The device showed a red light emission having a light emission brightness of 250 (cd/m$^2$) at a direct current voltage of 5 V, a maximum light emission brightness of 7,000 (cd/m$^2$) and a light emission efficiency of 0.7 (1 m/W).

Example 6

An organic EL device was obtained in the same manner as in Example 2 except that the light-emitting layer was replaced with a 30 nm thick light-emitting layer formed by vapor-depositing Compound (2) and Compound (49) in a Compound (2)/Compound (49) weight ratio of 100/3. The organic EL device showed a red light emission having a light emission brightness of 500 (cd/m$^2$) at a direct current voltage of 5 V, a maximum light emission brightness of 8,100 (cd/m$^2$) and a light emission efficiency of 0.9 (1 m/W).

Example 7

An organic EL device was obtained in the same manner as in Example 2 except that the light-emitting layer was replaced with a 30 nm thick light-emitting layer formed by vapor-depositing Compound (63) and Compound (61) in a Compound (63)/Compound (61) weight ratio of 100/5. The organic EL device showed a red light emission having a light emission brightness of 340 (cd/m$^2$) at a direct current voltage of 5 V, a maximum light emission brightness of 7,500 (cd/m$^2$) and a light emission efficiency of 1.0 (1 m/W).

Example 8

An organic EL device was obtained in the same manner as in Example 2 except that the light-emitting layer was replaced with a 30 nm thick light-emitting layer formed by vapor-depositing Compound (49) and α-NPD in a Compound (49)/α-NPD weight ratio of 5/100. The organic EL device showed an orange light emission having a light emission brightness of 420 (cd/m$^2$) at a direct current voltage of 5 V, a maximum light emission brightness of 12,000 (cd/m$^2$) and a light emission efficiency of 1.1 (1 m/W).

Example 9

An organic EL device was obtained in the same manner as in Example 2 except that the light-emitting layer was replaced with a 30 nm thick light-emitting layer formed by vapor-depositing Compound (53) and gallium bis(2-methyl-8-hydroxyquinolinate)(phenolate) complex in a Compound (53)/gallium bis(2-methyl-8-hydroxyquinolinate) (phenolate) complex weight ratio of 1/100. The organic EL device showed an orange light emission having a light emission brightness of 450 (cd/m$^2$) at a direct current voltage of 5 V, a maximum light emission brightness of 14,000 (cd/m$^2$) and a light emission efficiency of 1.3 (1 m/W).

Example 10

An organic EL device was obtained in the same manner as in Example 2 except that the light-emitting layer was replaced with a 30 nm thick light-emitting layer formed by vapor-depositing Compound (32) and Compound (49) in a Compound (32)/Compound (49) weight ratio of 100/1. The organic EL device showed a red light emission having a light emission brightness of 380 (cd/m$^2$) at a direct current voltage of 5 V, a maximum light emission brightness of 8,500 (cd/m$^2$) and a light emission efficiency of 0.9 (1 m/W).

Example 11

An organic EL device was obtained in the same manner as in Example 2 except that the light-emitting layer was replaced with a 30 nm thick light-emitting layer formed by vapor-depositing Compound (35) and Compound (49) in a Compound (35)/Compound (49) weight ratio of 100/3. The organic EL device showed a red light emission having a light emission brightness of 550 (cd/m$^2$) at a direct current voltage of 5 V, a maximum light emission brightness of 9,500 (cd/m$^2$) and a light emission efficiency of 0.9 (1 m/W).

Example 12

An organic EL device was obtained in the same manner as in Example 2 except that the light-emitting layer was replaced with a 30 nm thick light-emitting layer formed by vapor-depositing Compound (42) and Compound (53) in a Compound (42)/Compound (53) weight ratio of 100/3. The organic EL device showed a red light emission having a light emission brightness of 600 (cd/m$^2$) at a direct current voltage of 5 V, a maximum light emission brightness of 12,500 (cd/m$^2$) and a light emission efficiency of 1.1 (1 m/W).

Example 13

An organic EL device was obtained in the same manner as in Example 2 except that the light-emitting layer was replaced with a 30 nm thick light-emitting layer formed by vapor-depositing Compound (40) and Compound (61) in a Compound (40)/Compound (61) weight ratio of 100/3. The organic EL device showed a red light emission having a light emission brightness of 500 (cd/m$^2$) at a direct current voltage of 5 V, a maximum light emission brightness of 10,500 (cd/m$^2$) and a light emission efficiency of 1.0 (1 m/W).

Comparative Example 1

Compound (69) was vacuum-deposited on a cleaned glass substrate with an ITO electrode to form a hole-injecting type light emitting layer having a thickness of 50 nm. Then, a tris(8-hydroxyquinolinate) aluminum complex (Alq3) was vacuum-deposited to form an electron-injecting layer having a thickness of 30 nm. An electrode having a thickness of 100 nm was formed thereon from a magnesium/silver alloy having a magnesium/silver mixing weight ratio of 10/1, to obtain an organic EL device. The light emitting layer and the electron-injecting layer were deposited under vacuum at 10$^{-6}$ Torr at a substrate temperature of room temperature. The organic EL device showed an yellow light emission having a light emission brightness of 100 (cd/m$^2$) at a direct current voltage of 5 V, a maximum light emission brightness of 2,200 (cd/m$^2$) and a light emission efficiency of 0.2 (1 m/W). However, the light emission surface of the device had many dark spots, and the light emission life of the device was a few hours.

Compound (69)

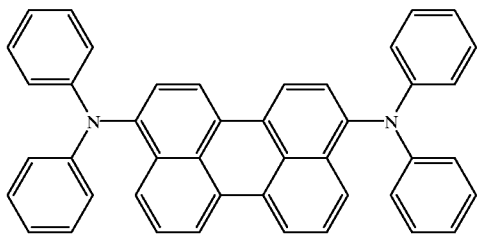

As is evident from the comparison of Comparative Example 1 and Example 1, extreme improvements were found in characteristics such as the maximum light emission brightness by introducing a substituent into a phenyl group.

The organic EL devices obtained in the above Examples, having the structure of at least 2 layers, showed a red light emission having a maximum light emission brightness of at least 4,000 (cd/m$^2$) and high light emission efficiency. Further, when the organic EL devices obtained in the above Examples were allowed to continuously emit light at (3 mA/cm$^2$), all the organic EL devices showed a stable light emission for more than 1,000 hours.

The organic EL device according to the present invention accomplishes improvements in light emission efficiency and brightness, and achieves an increased device life. There is therefore no limitation to be imposed on the light-emitting material, dopant, hole-injecting material, electron-injecting material, sensitizer, resin and electrode material which are used in combination with it, nor is the method of producing the device limited.

Effect of the Invention

The organic EL device using the organic EL device material of the present invention as a light emitting material shows a red light emission. According to the present invention, there can be obtained an organic EL device which exhibits a high light emission brightness with a high light emission efficiency and a long light emission life as compared with conventional organic EL devices.

What is claimed is:
1. A compound for a red light-emitting material for an organic electroluminescence device, which is a compound of the formula (1) and in which the maximum light emission wavelength is in a red light emission region:

(1)

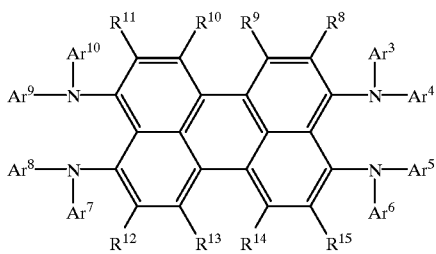

wherein each of Ar³ to A¹⁰ is independently a substituted or non-substituted aromatic monocyclic group, a substituted or non-substituted fused polycyclic group or a substituted or non-substituted aromatic heterocyclic group, provided that Ar³ and Ar⁴ may integrally bond to each other, that Ar⁵ and Ar⁶ may integrally bond to each other, that Ar⁷ and Ar⁸ may integrally bond to each other, that Ar⁹ and Ar¹⁰ may integrally bond to each other and each of R⁸ to R¹⁵ is independently a hydrogen atom of di(4-methylphenyl)amino.

2. A red light-emitting material for an organic electroluminescence device, which comprises the compound recited in claim 1.

3. The red light-emitting material according to claim 2, which contains the compound of the formula (1) and a host material, the content of the compound of the formula (1) being 0.001 to 50% by weight based on the host material.

4. The red light-emitting material according to claim 3, wherein the host material is at least one material selected from the group consisting of an electron-injecting material, a hole-injecting material and an electrically conductive polymer.

5. An organic electroluminescence device comprising a pair of electrodes composed of an anode and a cathode and an organic layer including at least one light-emitting layer, the organic layer being formed between a pair of the electrodes, the light-emitting layer containing the red light-emitting material recited in claim 2.

6. The organic electroluminescence device according to claim 5, wherein at least one electron-injecting layer is formed between the light-emitting layer and the cathode.

7. The organic electroluminescence device according to claim 6, wherein the light-emitting layer or the electron-injecting layer contains a compound of the formula (3)

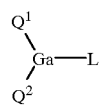

wherein each of Q¹ and Q² is independently a substituted or non-substituted hydroxyquinoline derivative or a substituted or non-substituted hydroxybenzoquinoline derivative, L is a halogen atom, a substituted or non-substituted alkyl group, a substituted or non-substituted cycloalkyl group, a substituted or non-substituted aryl group, a substituted or non-substituted aromatic heterocyclic group, or a ligand of —OR in which R is a hydrogen atom, a substituted or non-substituted alkyl group, a substituted or non-substituted cycloalkyl group, a substituted or non-substituted aryl group or a substituted or non-substituted aromatic heterocyclic group or —O—Ga—Q³ (Q⁴) in which Q³ and Q⁴ have the same meanings as those of Q¹ and Q².

8. A red light-emitting material according to claim 2, which is a mixture of at least two kinds of the compounds of the formula (1) or a mixture of at least one kind of compound of the formula (1) and at least one kind of compound of the formula (2):

(2)

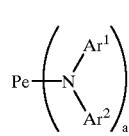

wherein Pe is a perylene residue, each of Ar¹ and Ar² is independently a substituted or non-substituted aryl group, a substituted or non-substituted fused polycyclic group, or a substituted or non-substituted aromatic heterocyclic group, provided that Ar¹ and Ar² may integrally bond to each other, and a is an integer of 2 to 12, provided that the compound of the formula (2) does not include the compound of the formula (1).

* * * * *